(12) United States Patent
Kawaura

(10) Patent No.: US 12,414,876 B2
(45) Date of Patent: Sep. 16, 2025

(54) COMPRESSION DEVICE SET AND METHOD FOR ATTACHING DEVICE

(71) Applicant: TERUMO KABUSHIKI KAISHA, Tokyo (JP)

(72) Inventor: Masakatsu Kawaura, Campbell, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 404 days.

(21) Appl. No.: 17/951,735

(22) Filed: Sep. 23, 2022

(65) Prior Publication Data

US 2023/0012524 A1 Jan. 19, 2023

Related U.S. Application Data

(63) Continuation of application No. PCT/JP2021/009087, filed on Mar. 8, 2021.

(30) Foreign Application Priority Data

Mar. 27, 2020 (JP) .................................. 2020-059037

(51) Int. Cl.
*A61F 13/02* (2024.01)
*A61F 13/00* (2024.01)
*A61F 13/0246* (2024.01)

(52) U.S. Cl.
CPC ........ *A61F 13/024* (2013.01); *A61F 13/0246* (2013.01); *A61F 2013/00412* (2013.01); *A61F 2013/00468* (2013.01)

(58) Field of Classification Search
CPC .... A61F 13/00; A61F 13/024; A61F 13/0246; A61F 2013/00412; A61F 2013/00468;
(Continued)

(56) References Cited

U.S. PATENT DOCUMENTS 697,637 A * 4/1902 Lee ...................... A61F 15/008
128/888
4,224,945 A * 9/1980 Cohen ............... A61F 13/00063
602/53
(Continued)

FOREIGN PATENT DOCUMENTS

CN 101106944 A 1/2008
CN 205913452 U 2/2017
(Continued)

OTHER PUBLICATIONS

International Search Report (PCT/ISA/210) with translation and Written Opinion (PCT/ISA/237) mailed on May 11, 2021, by the Japan Patent Office as the International Searching Authority for International Application No. PCT/JP2021/009087. (8 pages).

(Continued)

*Primary Examiner* — Tan-Uyen T Ho
*Assistant Examiner* — Osama Nemer
(74) *Attorney, Agent, or Firm* — BUCHANAN INGERSOLL & ROONEY PC

(57) ABSTRACT

A compression device set includes: a compression device to be adhered to a biological surface; and a cover member attachable to and detachable from the compression device. The compression device includes: an adhesive sheet having an adhesion lower surface to be adhered to the biological surface; and a compression member fixed to an upper surface side of the adhesive sheet and configured to compress the biological surface when the adhesion surface is adhered to the biological surface. The adhesive sheet includes a first portion that is in contact with the compression member and a second portion that is not in contact with the compression member. The cover member is configured to be attached to the compression member in a state in which the cover member is configured to come into contact with an (Continued)

upper surface of at least a part of the second portion of the adhesive sheet.

20 Claims, 21 Drawing Sheets

(58) Field of Classification Search
CPC .... A61M 2025/0246; A61M 2025/028; A61M 2025/0266; A61M 25/02; A61B 2017/00951; A61B 2017/0065; A61B 2017/00659; A61B 2017/12004; A61B 2017/00858; A61B 17/135; A61B 17/132; A61B 17/12; A61B 17/0057; A61B 17/1325; A61B 5/02233; A61H 39/04

See application file for complete search history.

(56) References Cited

U.S. PATENT DOCUMENTS

| | | | |
|---|---|---|---|
| 5,389,066 A | 2/1995 | Rhame, Jr. | |
| 5,507,721 A * | 4/1996 | Shippert | A61F 13/01034 |
| | | | 602/53 |
| 5,686,096 A * | 11/1997 | Khan | A61M 25/02 |
| | | | 424/443 |
| 9,265,665 B2 * | 2/2016 | Robinson | A61F 13/02 |
| 9,393,354 B2 * | 7/2016 | Freedman | A61M 1/77 |
| 9,439,827 B2 * | 9/2016 | Saatchi | A61H 1/006 |
| 10,117,979 B2 * | 11/2018 | Coulthard | A61F 13/02 |
| 10,888,334 B2 * | 1/2021 | Pancholy | A61B 5/0261 |
| 11,272,941 B1 * | 3/2022 | Buchanan | A61M 25/02 |
| 11,564,697 B2 * | 1/2023 | Pancholy | A61B 17/1325 |
| 11,839,464 B2 * | 12/2023 | Brownhill | A61N 1/0456 |
| 2009/0177083 A1 | 7/2009 | Matsumura | |
| 2009/0281565 A1 * | 11/2009 | McNeese | A61B 17/1325 |
| | | | 606/201 |
| 2009/0318952 A1 * | 12/2009 | Bates | A61B 17/12 |
| | | | 606/202 |
| 2012/0215252 A1 * | 8/2012 | Adenmark | A61B 17/135 |
| | | | 606/201 |
| 2015/0025436 A1 * | 1/2015 | Tang | A61F 13/0246 |
| | | | 602/43 |
| 2016/0058380 A1 * | 3/2016 | Lee | A61B 5/145 |
| | | | 600/365 |
| 2018/0008280 A1 * | 1/2018 | Clark | A61B 17/132 |
| 2021/0059686 A1 | 3/2021 | Kawaura et al. | |
| 2021/0186521 A1 * | 6/2021 | Kawaura | A61B 17/1325 |

FOREIGN PATENT DOCUMENTS

| | | |
|---|---|---|
| JP | H06327690 A | 11/1994 |
| JP | 2015505689 A | 2/2015 |
| JP | 2017047038 A | 3/2017 |
| JP | 2020116313 A | 8/2020 |
| WO | 2019221201 A1 | 11/2019 |
| WO | 2020050420 A1 | 3/2020 |

OTHER PUBLICATIONS

The extended European Search Report issued Jul. 12, 2023, by the European Patent Office in corresponding European Patent Application No. 21776410.9-1122. (7 pages).

Search Report issued on May 26, 2025, by thr State Intellectual Property Office in Chinese Patent Application No. 202180007758.6 and the First Office Action issued on May 30, 2025, by the State Intellectual Property Office in Chinese Patent Application No. 202180007758.6 and an English translation of the Action. (12 pages).

* cited by examiner

FIG.3
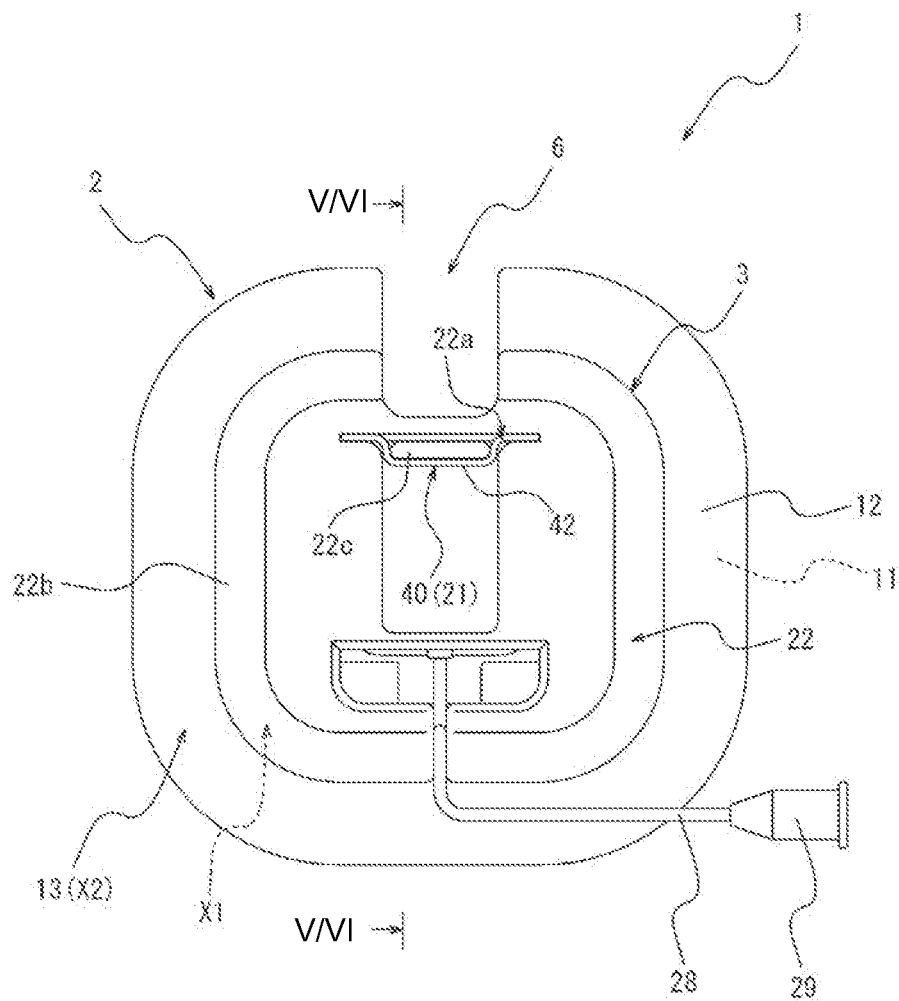
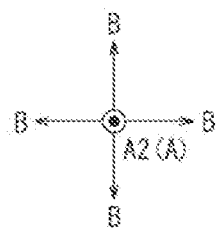

FIG.4
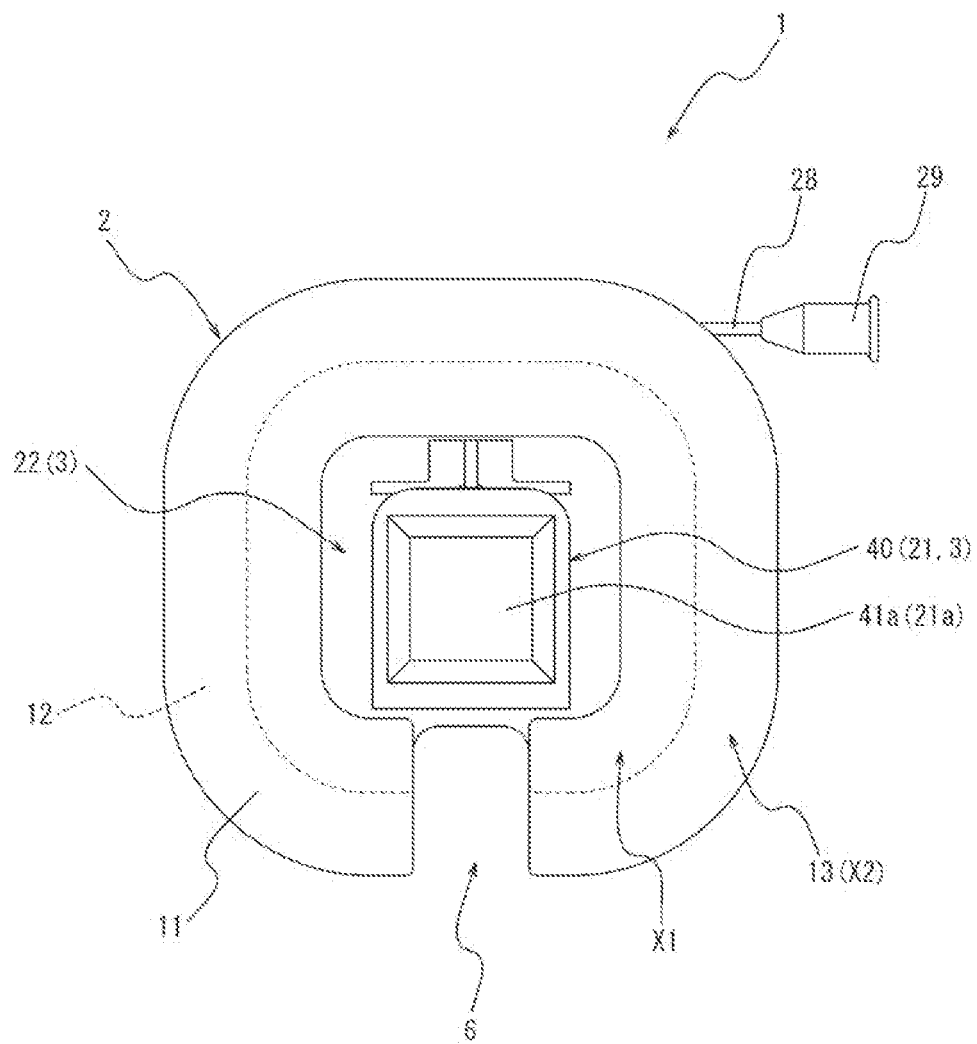
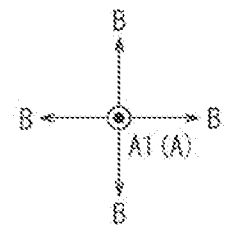

FIG. 7
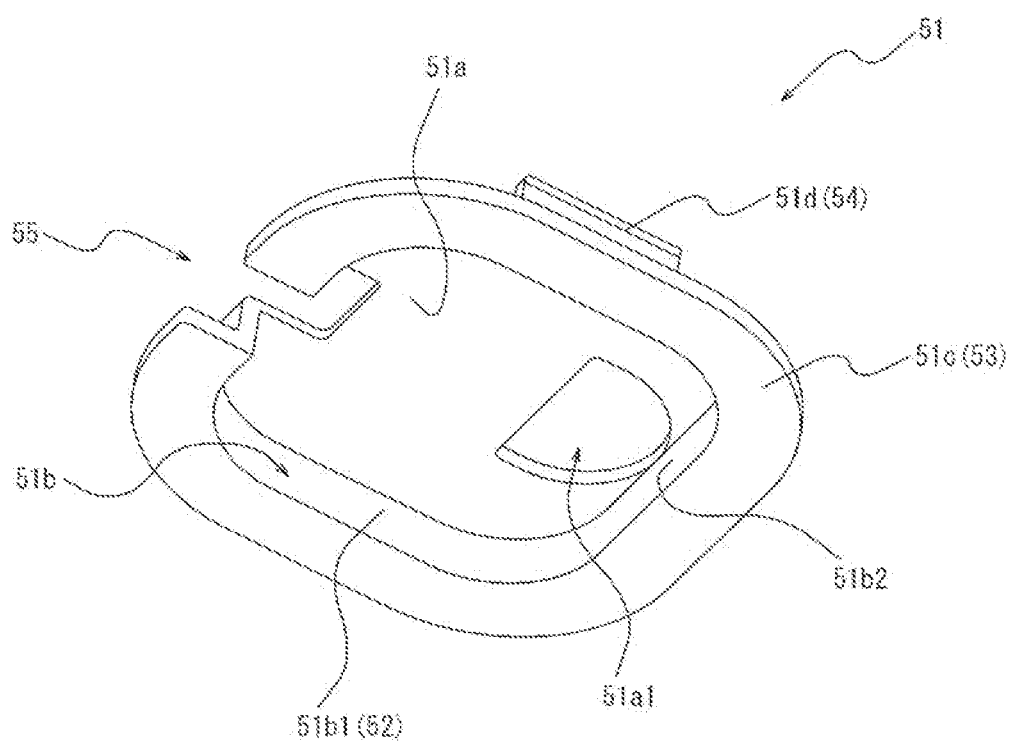

FIG.8
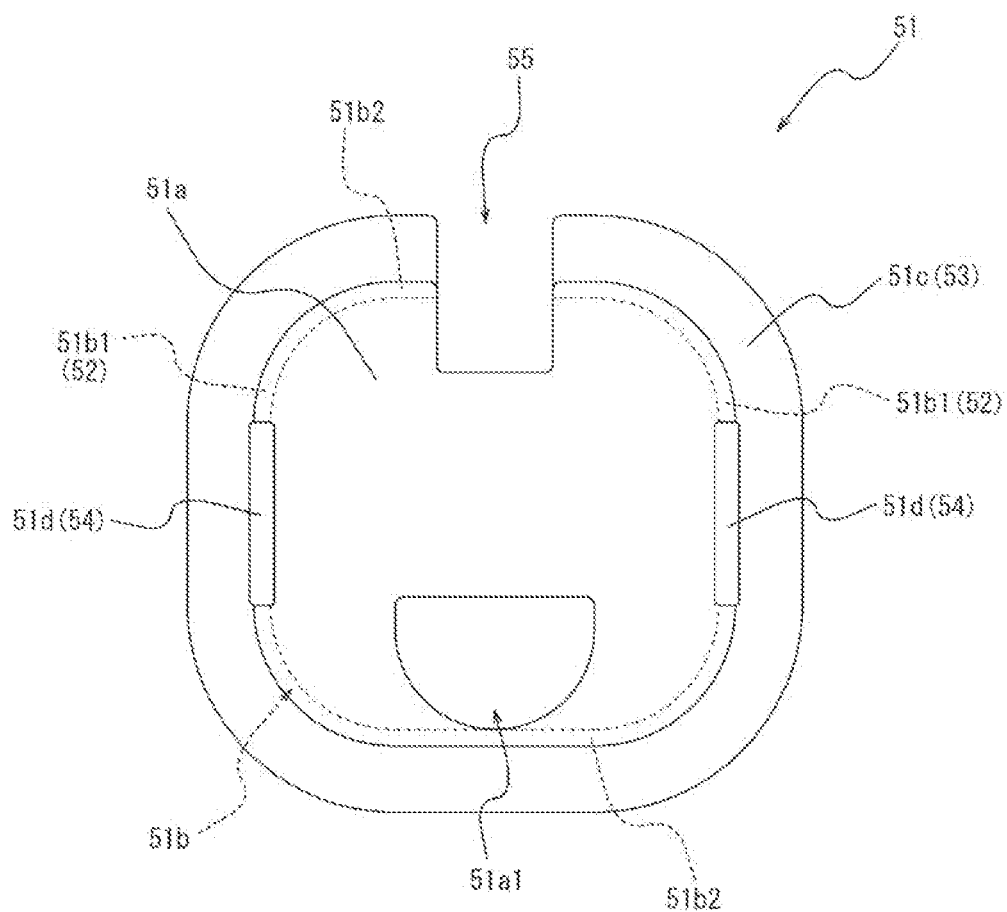
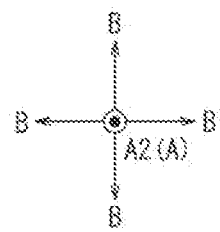

FIG.9
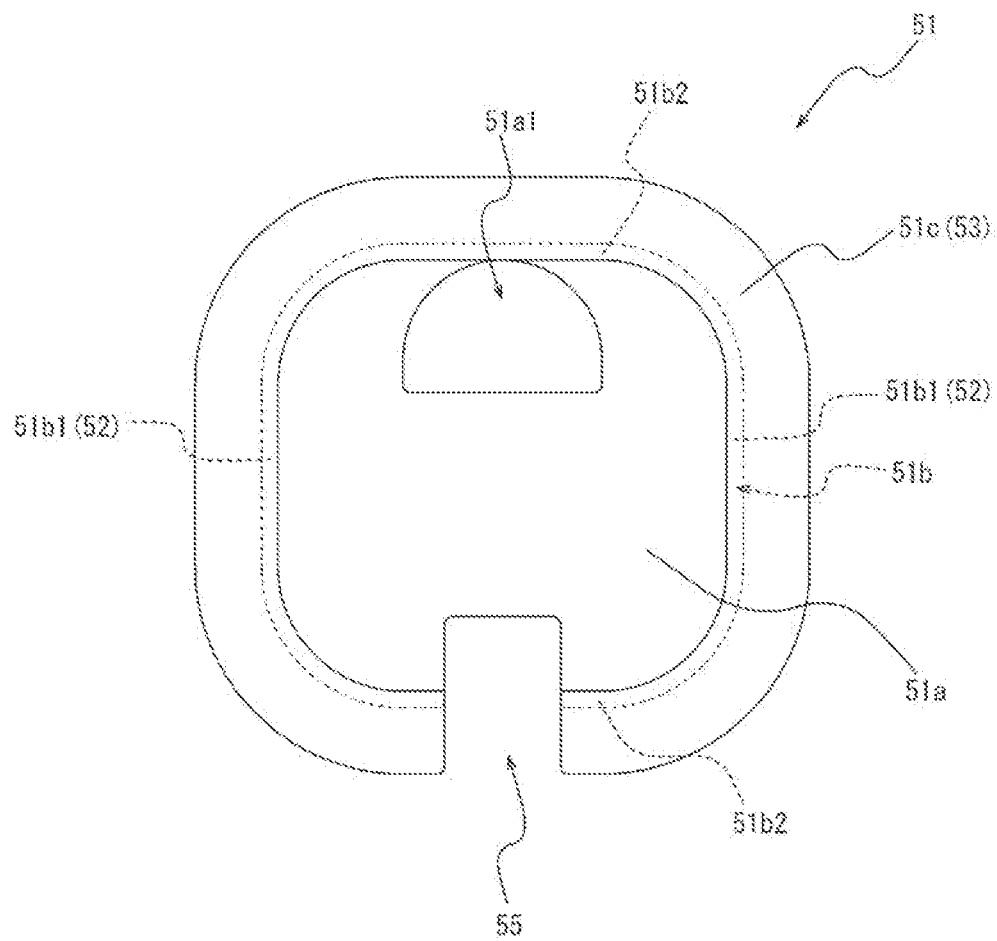
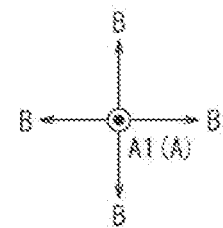

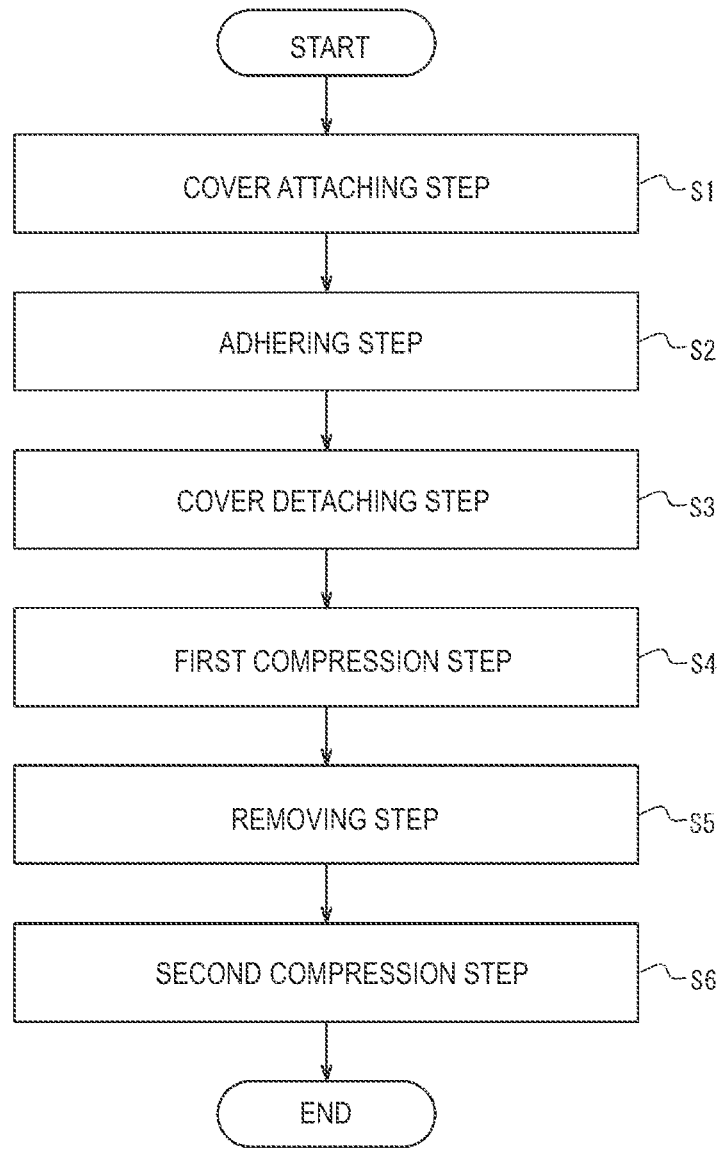

COMPRESSION DEVICE SET AND METHOD FOR ATTACHING DEVICE

CROSS-REFERENCES TO RELATED APPLICATIONS

This application is a continuation of International Patent Application No. PCT/JP2021/009087 filed on Mar. 8, 2021, which claims priority to Japanese Patent Application No. 2020-059037 filed on Mar. 27, 2020, the entire content of both of which is incorporated herein by reference.

TECHNOLOGICAL FIELD

This disclosure generally relates to a compression device set and a method for attaching a device.

BACKGROUND DISCUSSION

In recent years, in medical institutions, various forms of examinations or treatments are performed using elongated hollow tubular medical devices called catheters. A catheter is percutaneously inserted into a blood vessel from a puncture site formed at a wrist, an inguinal region, and the like, and is carried through the blood vessel to a site to be examined or treated. After an examination or treatment by a health care worker is completed, the catheter, or a sheath used to introduce the catheter, is removed from the puncture site, and the puncture site is stopped from bleeding.

International Patent Application Publication No. 2019/221201 (WO 2019/221201) discloses a compression device that compresses a wound of a patient or its vicinity after a sheath is removed. The compression device disclosed in the noted international application publication includes an adhesive sheet having an adhesion surface and a compression member attached to the adhesive sheet. The disclosed adhesive sheet includes a first portion to which a fixing portion of the compression member is fixed, and a second portion to which the fixing portion of the compression member is not fixed.

SUMMARY

The compression device disclosed in International Patent Application Publication No. 2019/221201 is unlikely to be released from a biological surface, since the adhesive sheet includes the second portion. However, the second portion of the adhesive sheet includes a portion that is not covered by the compression member. Therefore, when the compression device is attached to the biological surface, the portion of the second portion of the adhesive sheet which is not covered by the compression member is unlikely to be pressed against the biological surface. That is, in the compression device disclosed in the noted international patent application publication, there is still room for improvement from a viewpoint of operability when the second portion of the adhesive sheet is adhered to the biological surface.

Disclosed here are a compression device set and method for attaching a device that are capable of implementing a compression device that is easily attached to a biological surface and that is unlikely to be released from the biological surface.

According to a first aspect of this disclosure, a compression device set includes: a compression device that is configured to be adhered to a biological surface and that is configured to compress the biological surface; and a cover member configured to be attached to and detached from the compression device. The compression device includes: an adhesive sheet possessing a lower surface and possessing an upper surface side, with the lower surface of the adhesive sheet being an adhesion surface configured to be adhered to the biological surface; and a compression member that is fixed to the adhesive sheet on an upper surface side of the adhesive sheet and that is configured to compress the biological surface in a state in which the adhesion surface of the adhesive sheet is adhered to the biological surface. The adhesive sheet includes a first portion that is in contact with the compression member and a second portion that is not in contact with the compression member. The cover member is configured to be attached to the compression member in a state in which the cover member is configured to come into contact with an upper surface of at least a part of the second portion of the adhesive sheet.

According to one embodiment of this disclosure, the compression member of the compression device includes: an expander that is expandable; and a holding body configured to hold the expander to be expandable in a sheet thickness direction of the adhesive sheet, and the cover member is configured to be attached to the holding body.

According to one embodiment of this disclosure, the second portion of the adhesive sheet includes a peripheral portion located outside an outer edge of the holding body in a plan view seen in the sheet thickness direction, and the cover member is configured to be attached to the holding body in a state in which the cover member is configured to come into contact with an upper surface of the entire peripheral portion.

According to one embodiment of this disclosure, the cover member is locked to the holding body by engaging with a side end surface of the holding body, the side end surface being located in a sheet in-plane direction orthogonal to the sheet thickness direction.

According to one embodiment of this disclosure, the cover member includes: a clamping portion configured to clamp opposite portions of the side end surface of the holding body; and a sheet cover portion that protrudes from the clamping portion in the sheet in-plane direction and that is configured to come into contact with the upper surface of at least a part of the second portion of the adhesive sheet in the state in which the clamping portion clamps the opposite portions of the side end surface of the holding body.

According to one embodiment of this disclosure, the cover member includes a pair of gripping portions extending from the clamping portion in the sheet thickness direction, and by changing a facing distance between the pair of gripping portions, the cover member is switchable between a locking position at which the clamping portion clamps the opposite portions of the side end surface of the holding body and a locking release position at which the clamping portion does not clamp the opposite portions of the side end surface of the holding body.

According to one embodiment of this disclosure, the cover member includes: a side-end engaging portion that engages with each of the opposite portions of the side end surface of the holding body; and a sheet cover portion that protrudes from the side-end engaging portion in the sheet in-plane direction and that is configured to come into contact with the upper surface of at least a part of the second portion of the adhesive sheet in the state in which the side-end engaging portion engages with the opposite portions of the side end surface of the holding body, one of the side-end engaging portion and the opposite portions of the side end surface of the holding body is provided with a convex portion, and the other one of the side-end engaging portion and the opposite portions of the side end surface of the holding body is provided with a concave portion or a hole portion that is fitted with the convex portion.

According to one embodiment of this disclosure, the cover member includes a pair of gripping portions each extending in the sheet thickness direction from the side-end engaging portion, and by changing a facing distance between the pair of gripping portions, the cover member is switchable between a locking position at which the convex portion is fitted into the concave portions or the hole portions and a locking release position at which the convex portion is not fitted into the concave portion or the hole portion.

According to a second aspect of this disclosure, there is provided a method for attaching a compression device to a biological surface so that the compression device is operable to compress the biological surface. The compression device includes: an adhesive sheet possessing a lower surface and possessing an upper surface side, with the lower surface of the adhesive sheet being an adhesion surface configured to be adhered to the biological surface; and a compression member that is fixed to the adhesive sheet on an upper surface side of the adhesive sheet and that is configured to compress the biological surface in a state in which the adhesion surface of the adhesive sheet is adhered to the biological surface, the adhesive sheet includes a first portion that is in contact with the compression member and a second portion that is not in contact with the compression member. The method includes: an attaching step of attaching a cover member to the compression member in a state in which the cover member is configured to come into contact with an upper surface of at least a part of the second portion of the adhesive sheet; and an adhering step of pressing at least a part of the second portion of the adhesive sheet toward the biological surface via the cover member, and adhering at least the part of the second portion to the biological surface.

In accordance with another aspect, a compression device set comprises: a compression member and a cover member, with the compression member comprising an adhesive sheet, a holding member and an inflatable body. The adhesive sheet possesses an upper surface and also possesses a lower surface that is an adhesion surface configured to adhere the adhesive sheet to a biological surface. The holding member is fixed to the upper surface of the adhesive sheet so that a portion of the upper surface of the adhesive sheet is in contact with the holding member, with the holding member possessing a lower surface that faces toward the biological surface when the adhesive sheet is adhered to the biological surface. The inflatable body is fixed to the holding member and is positioned in underlying relation to the lower surface of the holding member so that the inflatable body is located between the lower surface of the holding member and the biological surface when the adhesive sheet is adhered to the biological surface. The inflatable body has an interior and an outer surface, and the inflatable body is expandable upon introducing a fluid into the interior of the inflatable body to press the outer surface of the inflatable body against a portion of the biological surface and apply a compression force to the portion of the biological surface when the adhesive sheet is adhered to the biological surface. The cover member is attachable to the compression member, and the cover member includes a surface configured to contact a part of the compression member when the cover member is attached to the compression member so that a force applied to the cover member is transmitted to the adhesive sheet of the compression member to press the adhesion surface of the adhesive sheet into adhering contact with the biological surface.

According to this disclosure, it is possible to provide the compression device set and the method for attaching the device that are capable of implementing the compression device that is easy to be attached to the biological surface and that is unlikely to be released from the biological surface.

BRIEF DESCRIPTION OF THE DRAWINGS

FIG. 3 is a top view of the compression device shown in FIG. 1.

FIG. 4 is a bottom view of the compression device shown in FIG. 1.

FIG. 7 is a perspective view of the cover member shown in FIG. 1 from a lower side.

FIG. 8 is a top view of the cover member shown in FIG. 1.

FIG. 9 is a bottom view of the cover member shown in FIG. 1.

FIG. 11 is a flowchart showing an example of a method for compressing a biological surface using the compression device shown in FIG. 1, the method including a method for attaching the compression device to the biological surface, according to one embodiment of this disclosure.

DETAILED DESCRIPTION

Figure 1:
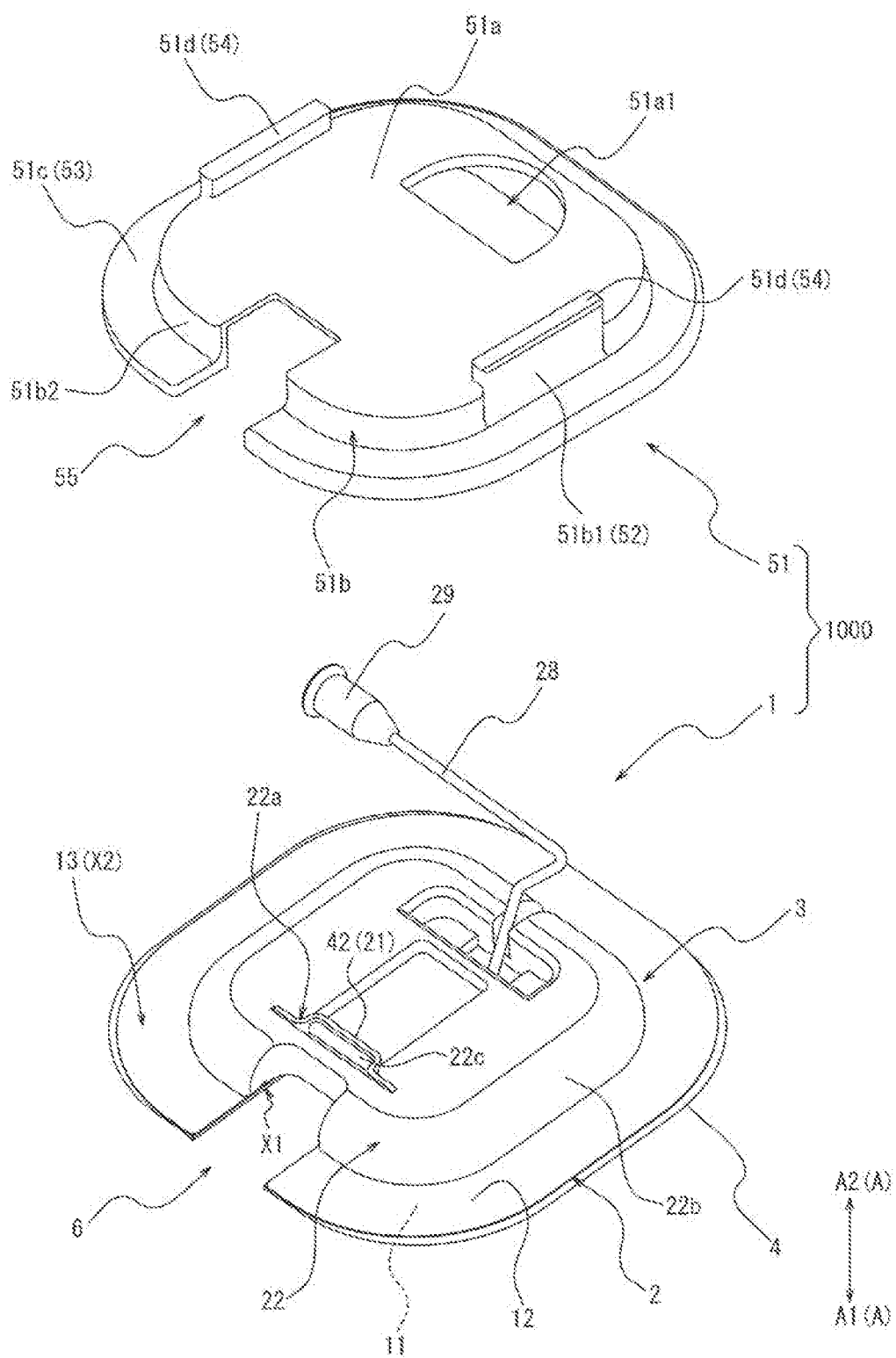
FIG. 1 is a perspective view of a compression device set in a state in which a cover member is not attached to a compression device according to one embodiment of this disclosure.

Set forth below with reference to the accompanying drawings is a detailed description of embodiments of a compression device and a method for attaching a device representing examples of the new compression device and method disclosed here. In the drawings, common members and portions are denoted by the same reference numerals.

Figure 2:
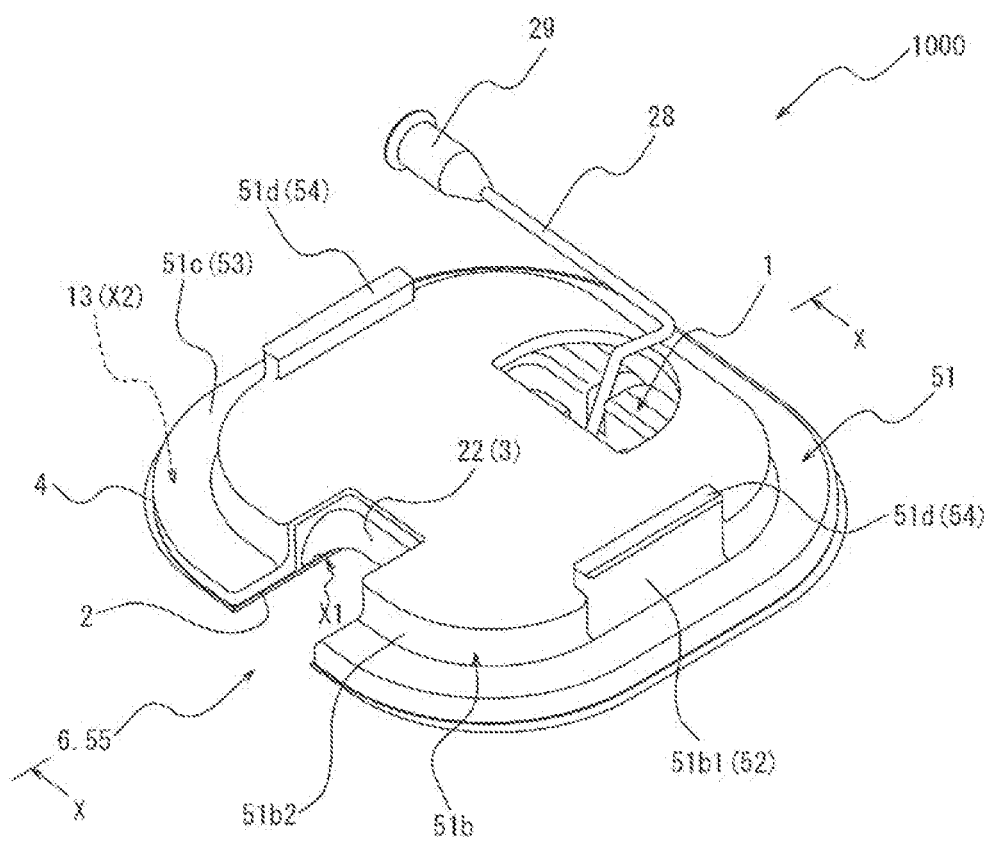
FIG. 2 is a perspective view of the compression device set shown in FIG. 1 in a state in which the cover member is detachably attached to the compression device.

FIG. 1 is a view showing a compression device set 1000 according to one embodiment of the compression device set according to this disclosure. As shown in FIG. 1, the compression device set 1000 includes a compression device 1 and a cover member 51. The cover member 51 can be attached to and detached from the compression device 1. FIG. 1 shows the compression device set 1000 in a state in which the cover member 51 is not attached to the compression device 1. FIG. 2 shows the compression device set 1000 in a state in which the cover member 51 is detachably attached to the compression device 1. FIGS. 1 and 2 show the compression device 1 in a state in which a release sheet 4 is attached to an adhesion surface 11 of an adhesive sheet 2. The release sheet 4 is released when the compression device 1 is attached to a biological surface.

[Compression Device 1]

Figure 5:
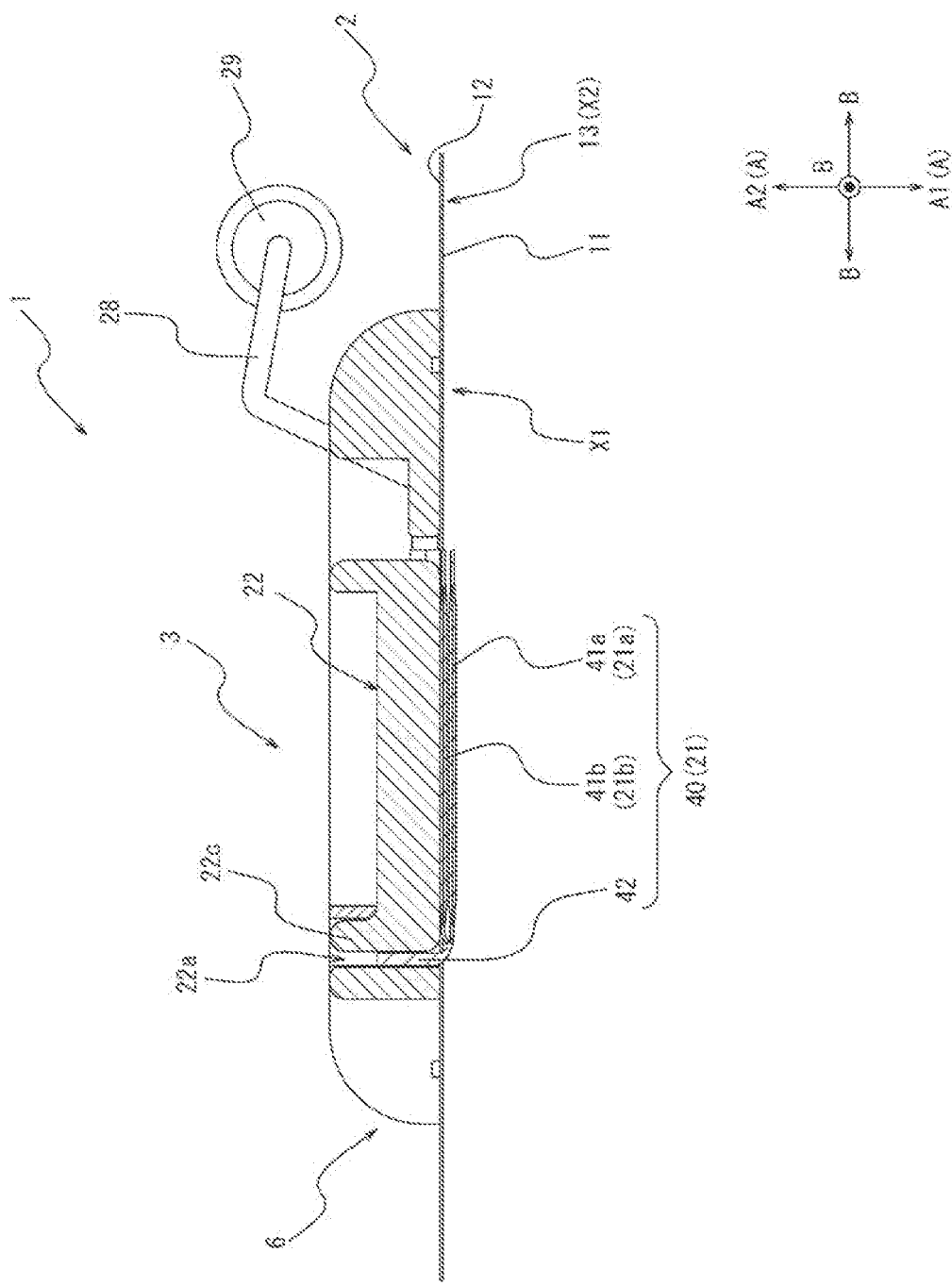
FIG. 5 is a cross-sectional view of the compression device shown in FIG. 1, taken along the section line V-V in FIG. 3, in a state in which an inflatable body is in a deflated form.
Figure 6:
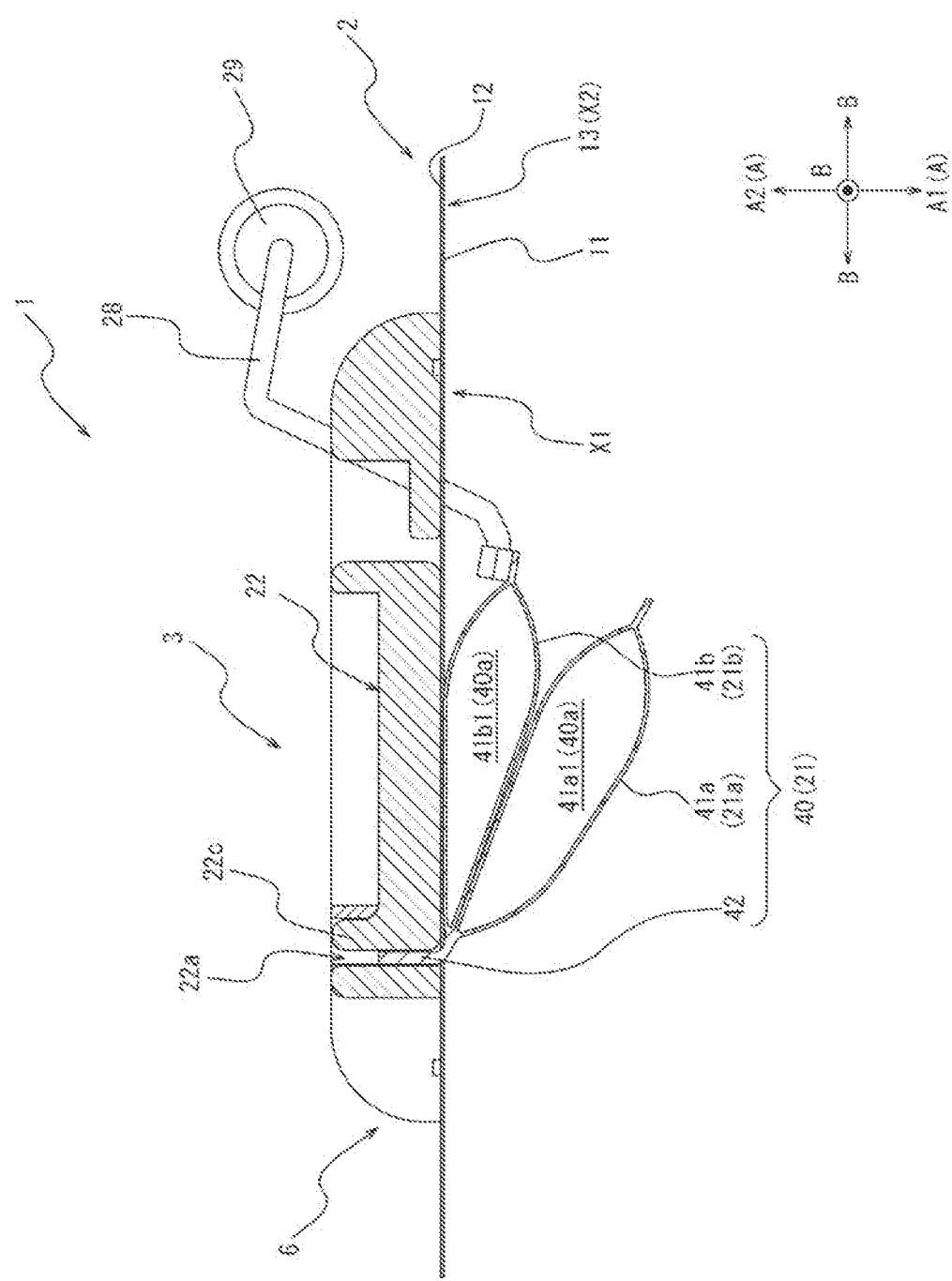
FIG. 6 is a cross-sectional view of the compression device shown in FIG. 1, taken along the section line VI-VI in FIG. 3, in a state in which the inflatable body is in an inflated form.

FIGS. 3 and 4 are plan views of the compression device 1. Specifically, FIG. 3 is a top view of the compression device 1. FIG. 4 is a bottom view of the compression device 1. FIGS. 5 and 6 are section views of the compression device 1 in a cross section taken along the section line V-V and VI-Vi respectively in FIG. 3. The details will be described later, and FIGS. 5 and 6 show different states of the compression device 1. In addition, FIGS. 3 to 6 show the compression device 1 in a state in which the release sheet 4 (see FIG. 1 or the like) is removed.

The compression device 1 can be adhered to the biological surface. In addition, the compression device 1 can compress the biological surface in a state of being adhered to the biological surface.

The compression device 1 includes the adhesive sheet 2 and a compression member 3.

The adhesive sheet 2 has, on a lower surface, the adhesion surface 11 that can be adhered to the biological surface. The compression member 3 is fixed to the adhesive sheet 2 on an upper surface side of the adhesive sheet 2. In addition, the compression member 3 can compress the biological surface in a state in which the adhesion surface 11 of the adhesive sheet 2 is adhered to the biological surface.

Accordingly, the compression device 1 is fixed to a position on the biological surface by adhering the adhesion surface 11 of the adhesive sheet 2 to the biological surface. In addition, the compression device 1 can compress a predetermined site on the biological surface by the compression member 3 in a state in which the compression device 1 is fixed to the position on the biological surface by the adhesion surface 11 of the adhesive sheet 2. A predetermined site on the biological surface includes, for example, a wound on the biological surface or its vicinity formed by inserting an elongated medical device such as a puncture needle, a catheter, and a sheath, from the biological surface, into a blood vessel of a living body. After the medical device is removed from the living body, bleeding can be stopped by compressing the wound on the biological surface or its vicinity by the compression member 3.

Hereinafter, the details of each member and each portion of the compression device 1 will be described.

<Adhesive Sheet 2>

The adhesive sheet 2 has the adhesion surface 11 on the lower surface located on one side in a sheet thickness direction A. In addition, the adhesive sheet 2 has, on an upper surface located on the other side in the sheet thickness direction A, an attaching surface 12 to which the compression member 3 is attached. The adhesive sheet 2 has flexibility. Therefore, the adhesive sheet 2 can be deformed according to a shape of the biological surface. That is, the adhesive sheet 2 can conform to a shape or contour of the biological surface. In addition, the adhesion surface 11 easily follows deformation of (i.e., conforms to) the biological surface. As a result, it is possible to prevent the compression device 1 from being unintentionally released from the biological surface.

Hereinafter, for convenience of description, the one side in the sheet thickness direction A, which is a direction from the attaching surface 12 to the adhesion surface 11 in the sheet thickness direction A, may be simply referred to as a "downward direction A1". In addition, for convenience of description, the other side in the sheet thickness direction A, which is a direction from the adhesion surface 11 to the attaching surface 12 in the sheet thickness direction A, may be simply referred to as an "upward direction A2". Further, in a plan view (see FIGS. 3 and 4) of the compression device 1 seen along the sheet thickness direction A of the adhesive sheet 2, a plan view (see FIG. 3) of the compression device 1 seen from an attaching surface 12 side of the adhesive sheet 2 may be simply referred to as a "top view" for convenience of description. In addition, in the plan view (see FIGS. 3 and 4) of the compression device 1 seen along the sheet thickness direction A of the adhesive sheet 2, a plan view (see FIG. 4) of the compression device 1 seen from an adhesion surface 11 side of the adhesive sheet 2 may be simply referred to as a "bottom view" for convenience of description. In addition, when the top view and the bottom view are not distinguished from each other, the "plan view" is simply referred to. In addition, unless otherwise specified, the simple descriptions of the "plan view", the "top view", and the "bottom view" mean a plan view, a top view, and a bottom view when an expander 21 of the compression member 3 to be described later is in a retracted form.

The adhesive sheet 2 includes a plurality of layers including, for example, a base material layer and an adhesive layer.

The base material layer is formed of, for example, a thin resin sheet. More specifically, the base material layer is formed of, for example, a white spunlace nonwoven fabric of polyester fibers, and has a thickness in a range of 5 µm to 150 µm, and for example, 30 µm. However, a material of the base material layer is not limited to polyester, and an acrylic polymer, polyethylene, an ethylene-vinyl acetate copolymer, polyurethane, a polyamide derivative, and the like may be used.

The adhesive layer is formed of an adhesive such as a rubber-based adhesive, an acrylic-based adhesive, and a silicon-based adhesive, for example. The adhesive layer is stacked on (overlies or overlaps) the base material layer directly or indirectly with another layer interposed therebetween. The adhesion surface 11 of the adhesive sheet 2 according to the present embodiment is an adhesive layer.

The adhesive sheet 2 may further include another layer in addition to the above-mentioned base material layer and the adhesive layer. The adhesive sheet 2 may include, for example, a surface layer. The surface layer is formed of, for example, a resin having a thickness of about 5 µm to 50 µm. More specifically, examples of a material of the surface layer include polyester, polyamide, polyamideimide, polyethylene, polypropylene, polycarbonate, polyurethane, polyvinyl chloride, and fluororesin. The surface layer is stacked on (overlies or overlaps) the base material layer directly or indirectly with another layer interposed therebetween on a side opposite to the adhesive layer with the base material layer interposed therebetween. Therefore, the attaching surface 12 of the adhesive sheet 2 may be a surface layer.

More specifically, the adhesive sheet 2 may be formed of, for example, a nonwoven fabric tape having an adhesive agent as an adhesive on one surface thereof. Further, the adhesive sheet 2 may be formed of, for example, a double-sided tape in which adhesive layers are provided on both sides of the base material layer. When the adhesive sheet 2 is formed of the double-sided tape, the compression member 3 can be fixed to the adhesive sheet 2 by being adhered to one adhesive layer of the adhesive sheet 2.

The adhesive sheet 2 according to the present embodiment extends in a C shape in the plan view shown in FIGS. 3 and 4. In other words, the adhesive sheet 2 according to the present embodiment defines a central opening region in the plan view. In the central opening region, a receiving portion 6 to be described later constitutes an open region communicating with the outside. The open region in the central opening region is a gap region sandwiched between both end portions of the C-shaped adhesive sheet 2 in the plan view.

As described above, the adhesive sheet 2 according to the present embodiment extends in the C shape in the plan view, but is not limited to the shape. The adhesive sheet 2 may have, for example, an endless (continuous) outer shape in the plan view. An outer edge shape and an inner edge shape of the endless adhesive sheet in the plan view are not particularly limited. The outer edge shape and the inner edge shape of the adhesive sheet having the endless outer shape in the plan view can be various shapes such as a circular shape, an oval shape, and a polygonal shape including a square shape.

In the adhesive sheet having the endless outer shape in the plan view, it is preferable that a slit extending from an outer edge to an inner edge is formed. By providing such a slit, the central opening region and the outside communicate with each other through the slit. Therefore, a medical device such as a catheter and a sheath can be moved from the outside of the adhesive sheet into the central opening region through the slit.

Next, a first portion X1 and a second portion X2 of the adhesive sheet 2 will be described.

As shown in FIGS. 3 and 4, and the like, the adhesive sheet 2 includes the first portion X1 that comes into contact with the compression member 3 and the second portion X2 that does not come into contact with the compression member 3. The first portion X1 means a region of the adhesive sheet 2 in a sheet in-plane direction B in which the compression member 3 comes into contact with the upper surface side. In addition, the second portion X2 means a region of the adhesive sheet 2 in the sheet in-plane direction B in which the compression member 3 does not come into contact with the upper surface side. Therefore, for example, if a portion is covered with the compression member 3 on the upper surface side and comes into contact with the compression member 3, the portion corresponds to the first portion X1 regardless of whether the compression member 3 is fixed. The adhesion surface 11 is provided in at least a part of a region of a lower surface of the first portion X1 and at least a part of a region of a lower surface of the second portion X2. More specifically, the adhesion surface 11 according to the present embodiment is provided on the entire lower surface of the first portion X1 and the entire lower surface of the second portion X2. That is, the adhesion surface 11 according to the present embodiment is provided on the entire lower surface of the adhesive sheet 2. Since the adhesive sheet 2 of the compression device 1 includes the second portion X2, it is possible to prevent the adhesive sheet 2 from being unintentionally released from the biological surface. The effect is based on the same principle as that described in International Patent Application Publication No. 2019/221201 mentioned above.

As shown in FIG. 3 or the like, the adhesive sheet 2 according to the present embodiment includes a peripheral portion 13 located on an outer periphery of the compression member 3 in the plan view. The peripheral portion 13 of the adhesive sheet 2 according to the present embodiment is the second portion X2 that does not come into contact with the compression member 3. In other words, the second portion X2 of the adhesive sheet 2 includes the peripheral portion 13 located outside an outer edge of a holding body 22, which will be described later, of the compression member 3 in the plan view.

As shown in FIG. 3 or the like, according to the present embodiment, the peripheral portion 13 of the adhesive sheet 2 does not surround the entire periphery of the compression member 3 in the plan view. That is, there is a position at which the peripheral portion 13 of the adhesive sheet 2 is not provided in the periphery of the compression member 3. At the position at which the peripheral portion 13 of the adhesive sheet 2 is not provided, a portion of the medical device such as a sheath inserted into the living body that extends outside the living body is received. That is, the receiving portion 6 that can receive the medical device such as a sheath is defined at the position at which the peripheral portion 13 of the adhesive sheet 2 is not provided in the periphery of the compression member 3. Accordingly, the compression device 1 can be attached to the biological surface in a state in which the portion of the medical device such as a sheath whose distal end side is inserted into (positioned or indwelled in) the living body which extends outside the living body is received by the receiving portion 6. Therefore, even in a state in which the medical device such as a sheath is inserted into the living body, it is easy to dispose the expander 21, which will be described later, of the compression member 3 such that the wound on the biological surface formed by the medical device or its vicinity is covered. That is, in such an arrangement state, the compression device 1 can be easily attached to the biological surface. As a result, in both the state in which the medical device such as a sheath is inserted into the living body and a state in which the medical device is removed from the living body, the wound on the biological surface or its vicinity is easily compressed by the expander 21 of the compression member 3 of the compression device 1.

<Compression Member 3>

The compression member 3 is fixed to the adhesive sheet 2 on the upper surface side of the adhesive sheet 2. Specifically, the compression member 3 according to the present embodiment is fixed to the attaching surface 12 of the adhesive sheet 2. In addition, the compression member 3 can compress the biological surface in a state in which the adhesion surface 11 of the adhesive sheet 2 is adhered to the biological surface. Specifically, the compression member 3 according to the present embodiment includes the expander 21 that is expandable and the holding body 22 that holds the expander 21 to be expandable in the sheet thickness direction A of the adhesive sheet 2.

As shown in FIGS. 3 and 4, and the like, the holding body 22 of the compression member 3 according to the present embodiment includes a portion that overlaps with the adhesive sheet 2 and a portion that does not overlap with the adhesive sheet 2 in the plan view. More specifically, the holding body 22 of the compression member 3 according to the present embodiment covers the central opening region of the adhesive sheet 2 in the plan view. A portion of the holding body 22 that overlaps with the central opening region in the plan view is the portion that does not overlap with the adhesive sheet 2. The holding body 22 according to the present embodiment covers the central opening region, and an outer edge portion of the holding body 22 in the plan view overlaps with the adhesive sheet 2. According to the present embodiment, the portion of the holding body 22 that overlaps with the adhesive sheet 2 in the plan view is in contact with and fixed to the attaching surface 12 of the adhesive sheet 2. Alternatively, the entire region of the portion of the holding body 22 that overlaps with the adhesive sheet 2 in the plan view may not be in contact with and fixed to the attaching surface 12 of the adhesive sheet 2. Therefore, only a small portion of the portion of the holding body 22 that overlaps with the adhesive sheet 2 in the plan view may be in contact with and fixed to the attaching surface 12 of the adhesive sheet 2. Therefore, the portion of the holding body 22 that overlaps with the adhesive sheet 2 in the plan view may include, for example, a portion that comes into contact with the attaching surface 12 of the adhesive sheet 2 but is not fixed thereto. The expander 21 according to the present embodiment, which will be described later, expands toward the downward direction A1 in the central opening region defined by the adhesive sheet 2 and can compress the biological surface.

The holding body 22 according to the present embodiment has a rounded square shape in the plan view and has a flat outer shape in the sheet thickness direction A. The holding body 22 covers a first inflatable portion 41a and a second inflatable portion 41b of an inflatable body 40 to be described later as the expander 21 in the upward direction A2. In addition, the holding body 22 is formed with a through hole 22a through which an extending portion 42 of the inflatable body 40 to be described later is inserted or positioned. Further, a locking protrusion 22c to which the extending portion 42 of the inflatable body 40 to be described later is locked is provided on an upper surface of the holding body 22.

Examples of a material of the holding body 22 include a resin material. Examples of the resin material include thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluororesin, polycarbonate, polyamide, acetal resin, acrylic resin, and polyethylene terephthalate, and thermosetting resins such as phenol resin, epoxy resin, silicone resin, and unsaturated polyester.

The expander 21 is held by the holding body 22. The expander 21 can protrude from the adhesion surface 11 of the adhesive sheet 2 toward the downward direction A1 as the one side in the sheet thickness direction A. In the compression device 1, the expander 21 protrudes in the downward direction A1 from the adhesion surface 11 of the adhesive sheet 2 in a state in which the adhesion surface 11 of the adhesive sheet 2 is adhered to the biological surface. Accordingly, the biological surface is compressed by the expander 21.

The expander 21 according to the present embodiment is the inflatable body 40 that can be inflated toward the downward direction A1 of the sheet thickness direction A by supplying a fluid such as air to the inflatable body 40 (interior of the inflatable body 40). When the inflatable body 40 according to the present embodiment is changed in form from a retracted form or deflated form as shown in FIG. 5 to a protruding form or inflated form as shown in FIG. 6, the inflatable body 40 protrudes toward the downward direction A1 from the adhesion surface 11 of the adhesive sheet 2 in the sheet thickness direction A, and is in a posture capable of compressing the biological surface.

Specifically, the compression device 1 according to the present embodiment is adhered to the biological surface in the retracted form (see FIG. 5) before the inflatable body 40 as the expander 21 is inflated. The inflatable body 40 is inflated by an operation of an operator such as a health care worker in a state in which the compression device 1 is fixed to the biological surface. The inflatable body 40 is inflated into the protruding form (see FIG. 6). The compression device 1 according to the present embodiment can compress the predetermined site on the biological surface by changing the inflatable body 40 from the retracted form to the protruding form. As described above, the predetermined site on the biological surface is a wound or the like formed by inserting a medical device such as a sheath into the living body. After the above-mentioned medical device such as a sheath is removed from the living body, bleeding can be stopped by compressing the wound on the biological surface or its vicinity with the inflatable body 40 as the expander 21 of the compression device 1. The details of a series of compression methods will be described later (see FIGS. 11 to 12F).

As shown in FIG. 5, the inflatable body 40 as the expander 21 according to the present embodiment is substantially flush with the adhesion surface 11 of the adhesive sheet 2 in the retracted form, and does not protrude from the adhesion surface 11 in the downward direction A1. The holding body 22 may include a locking mechanism that locks the inflatable body 40 so that the inflatable body 40 does not protrude from (beyond) the adhesion surface 11 of the adhesive sheet 2 in the downward direction A1 in the retracted form. As shown in FIG. 5, the inflatable body 40 is positioned in underlying relation to the holding body 22 (lower surface pf the holding body).

The inflatable body 40 according to the present embodiment defines internal spaces 40a. The internal spaces 40a of the inflatable body 40 communicate with a tube 28 that penetrates the holding body 22 and extends to the outside of the holding body 22. A fluid such as air is supplied through the tube 28 to the internal spaces 40a of the inflatable body 40 from a fluid supply device such as a syringe connected to an inflation port as a connection portion 29 provided at an end portion of the tube 28. Accordingly, the inflatable body 40 can be changed from the retracted form (see FIG. 5) to the protruding form (see FIG. 6). That is, the inflatable body 40 as the expander 21 can protrude from the adhesion surface 11 of the adhesive sheet 2 in the downward direction A1. The fluid supplied to the internal spaces of the inflatable body 40 is not limited to gas, and may be a liquid. In addition, by suctioning the fluid from the internal spaces 40a of the inflatable body 40, the inflatable body 40 can also be changed from the protruding form (see FIG. 6) to the retracted form (see FIG. 5).

More specifically, as shown in FIG. 6, the expander 21 according to the present embodiment includes a contact portion 21a that comes into contact with the biological surface and directly compresses the biological surface, and a pressing portion 21b that presses the contact portion 21a in a predetermined direction to increase a compression force of the contact portion 21a in the predetermined direction. Specifically, the inflatable body 40 as the expander 21 according to the present embodiment includes the first inflatable portion 41a as the contact portion 21a and the second inflatable portion 41b as the pressing portion 21b.

The first inflatable portion 41a defines a first internal space 41a1. The second inflatable portion 41b defines a second internal space 41b1. The first internal space 41a1 and the second internal space 41b1 communicate with each other. In the retracted form of the inflatable body 40, the first inflatable portion 41a and the second inflatable portion 41b that are in a deflated state overlap with each other in the sheet thickness direction A. The first inflatable portion 41a in the deflated state is located on a lower side, and the second inflatable portion 41b in the deflated state is overlapped on an upper side. The second inflatable portion 41b is covered with the holding body 22 in the upward direction A2. In addition, the first inflatable portion 41a and the second inflatable portion 41b are continuous only on one end side (left side in FIG. 6) in the sheet in-plane direction B orthogonal to the sheet thickness direction A.

The fluid supplied to the internal spaces 40a of the inflatable body 40 through the tube 28 flows into the second internal space 41b1 of the second inflatable portion 41b, and then flows into the first internal space 41a1 of the first inflatable portion 41a. Therefore, when the fluid is supplied to the internal spaces 40a of the inflatable body 40, the second inflatable portion 41b is first inflated. As described above, since the second inflatable portion 41b is covered by the holding body 22 in the upward direction A2, the second inflatable portion 41b to which the fluid is supplied is inflated in the downward direction A1. Next, the fluid flows into the first internal space 41a1 and the first inflatable portion 41a is inflated. At this time, the first inflatable portion 41a is inflated while pivoting about the one end side (left side in FIG. 6) in the sheet in-plane direction B continuous with the second inflatable portion 41b as a pivot center axis. That is, when the fluid is supplied to the first internal space 41a1 of the first inflatable portion 41a, the first inflatable portion 41a is pressed by the second inflatable portion 41b, and thus the first inflatable portion 41a is inflated such that the other end side (right side in FIG. 6) moves in the downward direction A1 with respect to the one end side in the sheet in-plane direction B, and the first inflatable portion 41a is in the protruding form shown in FIG. 6. Accordingly, a compression force in a predetermined direction (compression force in a lower left direction in FIG. 6) by the first inflatable portion 41a can be increased.

More specifically, the inflatable body 40 according to the present embodiment includes a sheet-shaped extending portion 42 extending from the first inflatable portion 41a and the second inflatable portion 41b. The first inflatable portion 41a and the second inflatable portion 41b according to the present embodiment are continuous with the extending portion 42 on a receiving portion 6 side in the sheet in-plane direction B in a cross-sectional view in FIGS. 5 and 6. At the time of inflation, the first inflatable portion 41a and the second inflatable portion 41b pivot about a portion of the extending portion 42 connected to the first inflatable portion 41a and the second inflatable portion 41b as a hinge portion. In other words, the first inflatable portion 41a and the second inflatable portion 41b can be inflated not only toward the sheet thickness direction A but also toward a direction inclined with respect to the sheet thickness direction A.

According to the present embodiment, the sheet-shaped extending portion 42 extending from a lower surface side to an upper surface side of the holding body 22 through the through hole 22a of the holding body 22 is fixed to the holding body 22 on the upper surface side of the holding body 22. Accordingly, the inflatable body 40 according to the present embodiment is locked to the holding body 22. More specifically, a slit is formed in the extending portion 42 according to the present embodiment. The locking protrusion 22c provided on the upper surface of the holding body 22 is inserted into or located in the slit. Accordingly, the extending portion 42 is positioned on the holding body 22.

More specifically, each of the first inflatable portion 41a and the second inflatable portion 41b according to the present embodiment is constituted by a balloon portion. As described above, the two balloon portions overlap with each other in the sheet thickness direction A. In addition, one end of each of the two balloon portions is attached to the extending portion 42. That is, the one end side of each of the two balloon portions is restrained by the extending portion 42. Therefore, even when the two balloon portions are inflated, the two balloon portions are not separated from each other on the one end side. On the other hand, the other end side of each of the two balloon portions is not restrained at all. Therefore, when the two balloon portions are inflated, the two balloon portions are separated from each other on the other end side. That is, in the two balloon portions constituting the first inflatable portion 41a and the second inflatable portion 41b according to the present embodiment, with the one end side attached to the extending portion 42 as a pivot center, the other end side which is not attached to the extending portion 42 pivots about the pivot center. Accordingly, the first inflatable portion 41a and the second inflatable portion 41b according to the present embodiment are inflated toward the direction inclined with respect to the sheet thickness direction A. Perforations P (see FIG. 13B) to be described later are easily narrowed or obstructed by inflating the inflatable body 40 toward the direction inclined with respect to the sheet thickness direction A. The details will be described later (see FIG. 14). The configuration for inflating the inflatable body 40 toward the direction inclined with respect to the sheet thickness direction A is not limited to a configuration of the expander 21 according to the present embodiment.

Materials that may be used to fabricate the balloon portions constituting the first inflatable portion 41a and the second inflatable portion 41b include, for example, soft polyvinyl chloride, polyurethane, polyethylene, polypropylene, polyester, ethylene-vinyl acetate copolymer (EVA), silicone, or a material having flexibility obtained by mixing any of these materials.

The configuration of the expander 21 is not particularly limited. The expander 21 may not have the pressing portion 21b. In addition, the expander 21 may not be an inflatable body. Further, even when the expander 21 is an inflatable body, the expander 21 is not limited to the configuration of the inflatable body 40.

[Cover Member 51]

Figure 10:
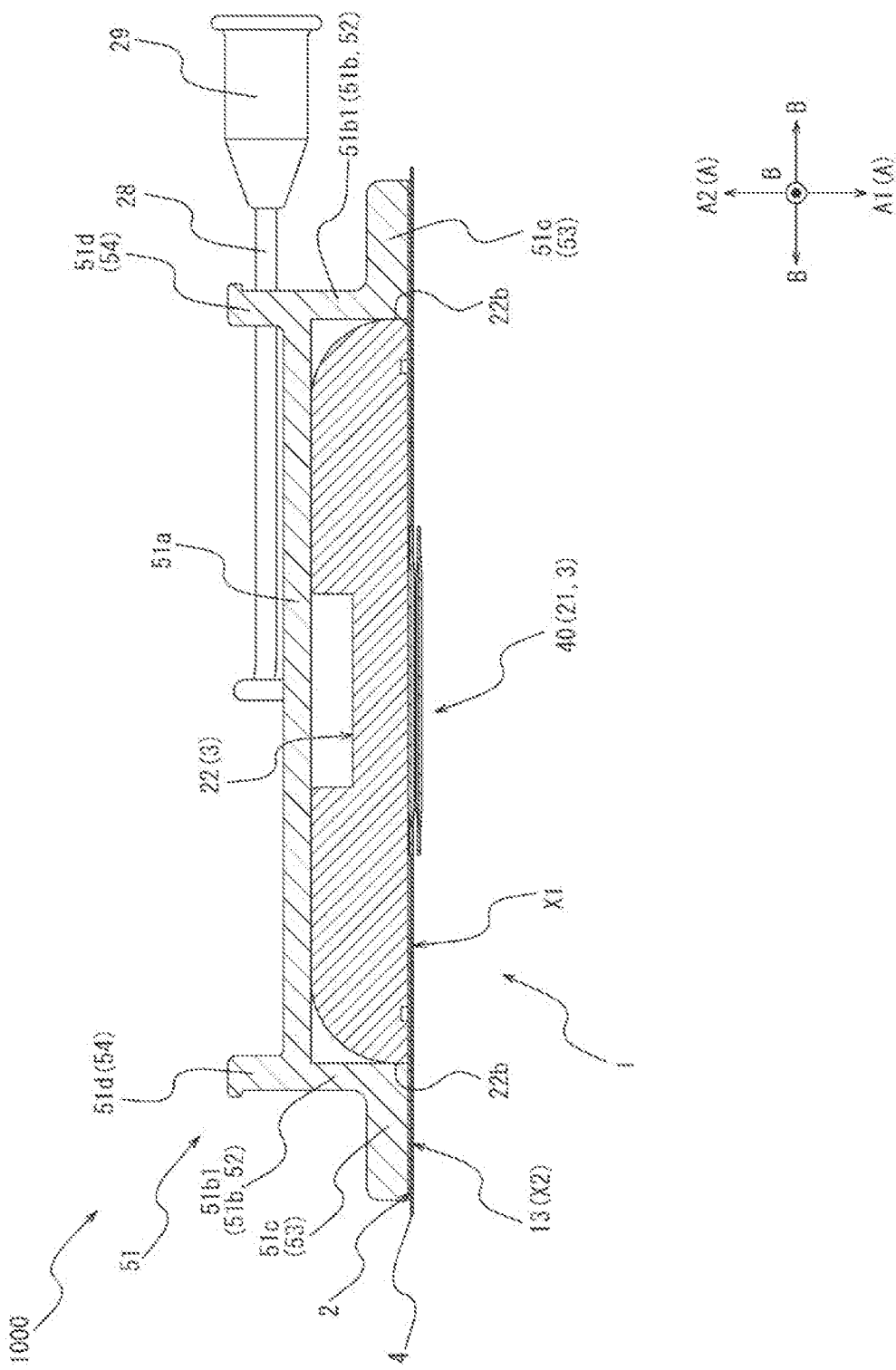
FIG. 10 is a cross-sectional view taken along a section line X-X in FIG. 2.

FIG. 7 is a perspective view of the cover member 51 seen from a lower side. FIG. 8 is a top view of the cover member 51. FIG. 9 is a bottom view of the cover member 51. FIG. 10 is a section view of the compression device set 1000 in a state in which the cover member 51 is attached to the compression device 1. Specifically, FIG. 10 is a section view taken along a line X-X in FIG. 2.

As shown in FIGS. 2 and 10, the cover member 51 can be attached to the compression member 3. In addition, as shown in FIG. 10, the cover member 51 can be attached to the compression member 3 in a state in which the cover member 51 comes into contact with an upper surface of at least a part of the second portion X2 of the adhesive sheet 2. Therefore, when the compression device 1 is pressed against the biological surface in a state in which the cover member 51 is attached to the compression device 1, the second portion X2 of the adhesive sheet 2 can be pressed toward the biological surface by the cover member 51. Accordingly, the adhesion surface 11 provided on the lower surface of the second portion X2 of the adhesive sheet 2 is also easily adhered to the biological surface. That is, the second portion X2 of the adhesive sheet 2, which is unlikely to be released from the biological surface after being adhered, is easily adhered to the biological surface. As a result, according to the compression device set 1000, it is possible to implement the compression device 1 that is easily attached to the biological surface and that is unlikely to be released from the biological surface.

Alternatively, the cover member 51 may be attached to the compression member 3 in a state in which the cover member 51 may come into contact with the upper surface of at least a part of the second portion X2 of the adhesive sheet 2. That is, in a state in which the cover member 51 is attached to the compression member 3, the cover member 51 may not be in constant contact with the upper surface of at least a part of the second portion X2 of the adhesive sheet 2. In such a case, the cover member 51 may come into contact with the upper surface of at least a part of the second portion X2 of the adhesive sheet 2. As an example, in a state in which the cover member 51 is attached to the compression device 1, a part of the cover member 51 (for example, a flange plate portion 51c as a sheet cover portion 53 to be described later according to the present embodiment) can be elastically deformed. By elastically deforming a part of the cover member 51, the part may come into contact with the upper surface of at least a part of the second portion X2 of the adhesive sheet 2.

By using the cover member 51 that can be attached to and detached from the compression member 3, a thickness of the compression member 3 in the sheet thickness direction A can be reduced. Accordingly, a burden on a patient due to the compression device 1 placed on the biological surface can be reduced.

The cover member 51 according to the present embodiment can be attached to the holding body 22 of the compression member 3. In addition, the cover member 51 according to the present embodiment cannot be attached to the expander 21 of the compression member 3. Accordingly, an attaching position and an attaching posture of the cover member 51 with respect to the compression member 3 are unlikely to change. Therefore, the cover member 51 can be more reliably attached to the compression member 3 regardless of a change in the form of the expander 21. In addition, a state in which the cover member 51 is attached to and integrated with the compression member 3 can be further stabilized. As a result, it is possible to prevent the cover member 51 from being unintentionally detached from the compression member 3.

The cover member 51 according to the present embodiment can be attached to the holding body 22 of the compression member 3 in a state in which the cover member 51 comes into contact with an upper surface of the entire region of the peripheral portion 13 of the second portion X2 of the adhesive sheet 2. Accordingly, the entire adhesion surface 11 provided on a lower surface of the peripheral portion 13 can be more reliably adhered to the biological surface. As a result, it is possible to further prevent the compression device 1 from being released from the biological surface.

As shown in FIG. 10, the cover member 51 is locked to the holding body 22 by engaging with a side end surface 22b of the holding body 22 that is located in the sheet in-plane direction B orthogonal to the sheet thickness direction A. Accordingly, when the cover member 51 is engaged with the side end surface 22b of the holding body 22, the cover member 51 is also easily flattened.

More specifically, as shown in FIG. 10, the cover member 51 according to the present embodiment includes a clamping portion 52, the sheet cover portion 53, and a pair of gripping portions 54.

The clamping portion 52 can clamp opposite portions of the side end surface 22b of the holding body 22. The cover member 51 is locked to the compression device 1 by clamping the opposite portions of the side end surface 22b of the holding body 22 with the clamping portion 52.

More specifically, the cover member 51 according to the present embodiment includes a ceiling plate portion (cover plate portion) 51a having a rounded square shape with which the upper surface of the holding body 22 is covered, and a peripheral wall portion 51b that protrudes from an outer edge of the ceiling plate portion 51a to one side of the ceiling plate portion 51a in a thickness direction. The peripheral wall portion 51b includes a pair of first plate portions 51b1 (seen in FIGS. 7 and 10) that protrude from facing portions of the outer edge of the ceiling plate portion 51a and that face each other. In addition, the peripheral wall portion 51b includes a pair of second plate portions 51b2 (seen in FIG. 10) that protrude from portions of the outer edge of the ceiling plate portion 51a that are different from the portions from which the pair of first plate portions 51b1 protrude. The pair of second plate portions 51b2 face each other. In a plan view of the ceiling plate portion 51a seen in the thickness direction, the pair of second plate portions 51b2 extend in a direction substantially orthogonal to the pair of first plate portions 51b1. The thickness direction of the ceiling plate portion 51a of the cover member 51 coincides with the sheet thickness direction A in a state in which the cover member 51 is attached to the compression device 1 (see FIG. 2). Hereinafter, as shown in FIGS. 1 and 2, a state in which the cover member 51 is located in the upward direction A2 with respect to the compression device 1 and the ceiling plate portion 51a of the cover member 51 coincides with the sheet thickness direction A will be described as a reference. Therefore, hereinafter, the thickness direction of the ceiling plate portion 51a of the cover member 51 is simply referred to as the "sheet thickness direction A". In addition, in the thickness direction of the ceiling plate portion 51a of the cover member 51, a side on which the compression device 1 is located is referred to as the "downward direction A1", and an opposite side thereof is referred to as the "upward direction A2". Further, a plan view of the cover member 51 seen from the thickness direction of the ceiling plate portion 51a is also hereinafter simply referred to as a "plan view". In addition, hereinafter, for convenience of description, the state in which the cover member 51 is attached to the compression device 1 is simply referred to as an "attached state".

The above-mentioned clamping portion 52 according to the present embodiment is constituted by the pair of first plate portions 51b1. The cover member 51 according to the present embodiment is covered from an upper side of the compression device 1 toward the downward direction A1. By the operation, the pair of first plate portions 51b1 as the clamping portion 52 move in the downward direction A1 while sliding with the opposite portions of the side end surface 22b of the holding body 22 of the compression member 3. The cover member 51 can move in the downward direction A1 until a lower surface of the ceiling plate portion 51a abuts on the upper surface of the holding body 22. When the cover member 51 reaches a position where the cover member 51 cannot move in the downward direction A1 with respect to the holding body 22, the attachment of the cover member 51 to the compression device 1 is completed and the cover member 51 is in the attached state.

As shown in FIG. 10, according to the present embodiment, the cover member 51 is locked to the compression device 1 by clamping the opposite portions of the side end surface 22b of the holding body 22 with the pair of first plate portions 51b1. Alternatively, not only the pair of first plate portions 51b1 but also the pair of second plate portions 51b2 may clamp the other opposite portions of the side end surface 22b of the holding body 22.

According to the present embodiment, the cover member 51 clamps the side end surface 22b of the holding body 22. Accordingly, the cover member 51 is locked to the compression device 1. With such a configuration, a mechanism that makes the cover member 51 attached to and detached from the compression device 1 can be implemented by a simple configuration.

The ceiling plate portion 51a according to the present embodiment is formed with a ceiling plate opening 51a1 through which the tube 28 of the compression device 1 is inserted in the attached state.

The sheet cover portion 53 protrudes from the clamping portion 52 in the sheet in-plane direction B. The sheet cover portion 53 according to the present embodiment is in contact with the upper surface of at least a part of the second portion X2 of the adhesive sheet 2 in the attached state. More specifically, the sheet cover portion 53 according to the present embodiment is in contact with the upper surface of the entire peripheral portion 13 of the second portion X2 of the adhesive sheet 2 in the attached state. Therefore, when the compression device 1 is adhered to the biological surface by using the compression device set 1000, the entire peripheral portion 13 of the adhesive sheet 2 can be pressed toward the biological surface by the sheet cover portion 53 of the cover member 51. Accordingly, the peripheral portion 13 of the adhesive sheet 2 can be more reliably attached to the biological surface.

More specifically, the cover member 51 according to the present embodiment includes the flange plate portion 51c extending outward from the peripheral wall portion 51b substantially parallel to the ceiling plate portion 51a from a lower end of the peripheral wall portion 51b. The sheet cover portion 53 according to the present embodiment is constituted by the flange plate portion 51c.

As described above, the flange plate portion 51c as the sheet cover portion 53 according to the present embodiment comes into contact with the upper surface of the second portion X2 of the adhesive sheet 2 in the attached state, but is not limited thereto. The sheet cover portion 53 may come into contact with the upper surface of the second portion X2 of the adhesive sheet 2 even when the sheet cover portion 53 is not in contact with the upper surface of the second portion X2 in the attached state. The flange plate portion 51c as the sheet cover portion 53 may be elastically deformed in the sheet thickness direction A and oscillated with a portion connected to the peripheral wall portion 51b as a fulcrum. In such a case, the flange plate portion 51c may not be in constant contact with the upper surface of the peripheral portion 13 of the adhesive sheet 2 in the attached state. The flange plate portion 51c can come into contact with the upper surface of the peripheral portion 13 of the adhesive sheet 2 by being pressed in the downward direction A1 and elastically deformed.

According to the present embodiment, a state in which the lower surface of the ceiling plate portion 51a of the cover member 51 is in contact with the upper surface of the holding body 22 and a lower surface of the flange plate portion 51c of the cover member 51 is in contact with the upper surface of the peripheral portion 13 of the adhesive sheet 2 is defined as an attached state. However, the attached state is not limited to the above-mentioned contact relationship. The attached state may be defined only by whether the lower surface of the ceiling plate portion 51a of the cover member 51 is in contact with the upper surface of the holding body 22. In addition, the attached state may be defined only by whether the sheet cover portion 53 of the cover member 51 is in contact with the second portion X2 of the adhesive sheet 2. Further, the attached state may be defined by a contact state of another portion.

The pair of gripping portions 54 extend from the clamping portion 52 in the sheet thickness direction A. Specifically, the pair of gripping portions (upstanding gripping portions) 54 according to the present embodiment are constituted by a pair of gripping plate portions 51d each extending in the upward direction A2 from each one of the pair of first plate portions 51b1 as the clamping portion 52. In other words, the pair of gripping plate portions 51d protrude from the outer edge of the ceiling plate portion 51a toward a direction (upward direction A2 according to the present embodiment) opposite to a direction in which the pair of first plate portions 51b1 protrude in the sheet thickness direction A.

By operating (e.g., gripping/releasing) the pair of gripping plate portions 51d as the pair of gripping portions 54, the health care worker can elastically deform the cover member 51 and change a facing distance between the pair of gripping plate portions 51d. According to the present embodiment, when the cover member 51 is deformed such that the facing distance between the pair of gripping plate portions 51d decreases, a facing distance between the pair of first plate portions 51b1 located on sides opposite to the pair of gripping plate portions 51d with the ceiling plate portion 51a interposed therebetween increases. On the other hand, according to the present embodiment, when the cover member 51 is deformed such that the facing distance between the pair of gripping plate portions 51d increases, the facing distance between the pair of first plate portions 51b1 decreases. As described above, according to the present embodiment, the facing distance of the clamping portion 52 can be changed by changing the facing distance between the pair of gripping portions 54. Therefore, by operating the pair of gripping portions 54, the facing distance of the clamping portion 52 can be changed, and an engaging relationship between the clamping portion 52 and the holding body 22 can be changed. That is, by changing the facing distance between the pair of gripping portions 54, it is possible to switch between a locking position at which the clamping portion 52 contacts and clamps the opposite portions of the side end surface 22b of the holding body 22 and a locking release position at which the clamping portion 52 does not clamp the opposite portions of the side end surface 22b of the holding body 22.

More specifically, according to the present embodiment, when the pair of gripping plate portions 51d as the pair of gripping portions 54 are sandwiched, the ceiling plate portion 51a bends and deforms toward the upward direction A2, which is an out-of-plane direction. Accordingly, the facing distance between the pair of first plate portions 51b1 as the clamping portion 52 can be increased. On the other hand, by releasing a force for sandwiching the pair of gripping plate portions 51d as the pair of gripping portions 54, the bent and deformed ceiling plate portion 51a returns to a flat plate shape by a recovering force. Accordingly, the facing distance between the pair of first plate portions 51b1 as the clamping portion 52 can be returned, that is, decreased.

According to the present embodiment, the facing distance between the pair of first plate portions 51b1 as the clamping portion 52 is changed by bending and deforming the ceiling plate portion 51a of the cover member 51, but this disclosure is not limited thereto. That is, the facing distance between the pair of first plate portions 51b1 as the clamping portion 52 may be changed by another configuration. For example, a portion other than the ceiling plate portion 51a may be deformed. However, according to the present embodiment, it is preferable that when the cover member 51 is elastically deformed by changing the facing distance between the pair of gripping portions 54, the locking position and the locking release position are switched as described above. In this way, it is possible to switch between the locking position and the locking release position with a simple configuration.

As shown in FIGS. 1 and 2, and the like, the cover member 51 according to the present embodiment is formed with a receiving portion 55. Specifically, the flange plate portion 51c of the cover member 51 does not surround the entire periphery of the ceiling plate portion 51a in the plan view. That is, there is a position at which the flange plate portion 51c is not provided in the periphery of the ceiling plate portion 51a in the plan view. At the position at which the flange plate portion 51c is not provided, a portion of a medical device such as a sheath inserted into or positioned in the living body that extends outside the living body is received. That is, the receiving portion 55 that can receive the medical device such as a sheath is provided at the position at which the flange plate portion 51c is not provided in the periphery of the ceiling plate portion 51a in the plan view. As shown in FIGS. 1 and 2 and FIGS. 7 to 9, the receiving portion 55 according to the present embodiment is constituted by a notch portion formed at an outer edge of the cover member 51. The notch portion constituting the receiving portion 55 is formed from an outer edge of the flange plate portion 51c of the cover member 51 to the peripheral wall portion 51b and the ceiling plate portion 51a. In other words, the flange plate portion 51c and peripheral wall portion 51b are not provided at a position at which the receiving portion 55 according to the present embodiment is provided. At the position at which the receiving portion 55 according to the present embodiment is provided, a concave portion is formed at the outer edge of the ceiling plate portion 51a.

The receiving portion 55 is aligned to overlap with the receiving portion 6 of the compression device 1 in the sheet thickness direction A. That is, the cover member 51 is attached to the compression device 1 in a state in which the receiving portion 55 and the receiving portion 6 are aligned to overlap each other in the sheet thickness direction A. On the other hand, by such alignment and attachment, the above-mentioned clamping portion 52 can clamp the holding body 22 of the compression member 3 at an appropriate position.

Since the cover member 51 is provided with the receiving portion 55, the portion of the medical device such as a sheath whose distal end side is inserted into the living body, which extends outside the living body, can be received not only by the receiving portion 6 of the compression device 1 but also by the receiving portion 55 of the cover member 51. Therefore, the compression device 1 can be easily positioned on the biological surface such that the wound on the biological surface formed by the medical device such as a sheath inserted into the living body or its vicinity is covered with the expander 21 of the compression member 3. Further, the compression device 1 can be attached to the biological surface in the positioned state. Therefore, even when the medical device such as a sheath is inserted into the living body, the compression device 1 can be attached to an appropriate position on the biological surface while the cover member 51 is attached to the compression device 1. As a result, in both the state in which the medical device such as a sheath is inserted into the living body and the state in which the medical device is removed from the living body, the wound on the biological surface or its vicinity can be compressed by the expander 21 of the compression member 3 of the compression device 1.

A configuration of the cover member 51 is not particularly limited as long as the cover member 51 can be attached to the compression member 3 in the state in which the cover member 51 can come into contact the upper surface of at least a part of the second portion X2 of the adhesive sheet 2. Therefore, for example, an outer shape of each portion of the cover member 51 in the plan view is not particularly limited. The ceiling plate portion 51a, the peripheral wall portion 51b, and the flange plate portion 51c according to the present embodiment may all be appropriately configured according to an outer shape of the compression device 1.

Examples of a material of the cover member 51 include a resin material. Examples of the resin material include thermoplastic resins used in injection molding such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxyethylene, fluororesin, polycarbonate, polyamide, acetal resin, acrylic resin, and polyethylene terephthalate, and thermosetting resins such as phenol resin, epoxy resin, silicone resin, and unsaturated polyester.

<Compression Method Using Compression Device 1>

Figure 12A:
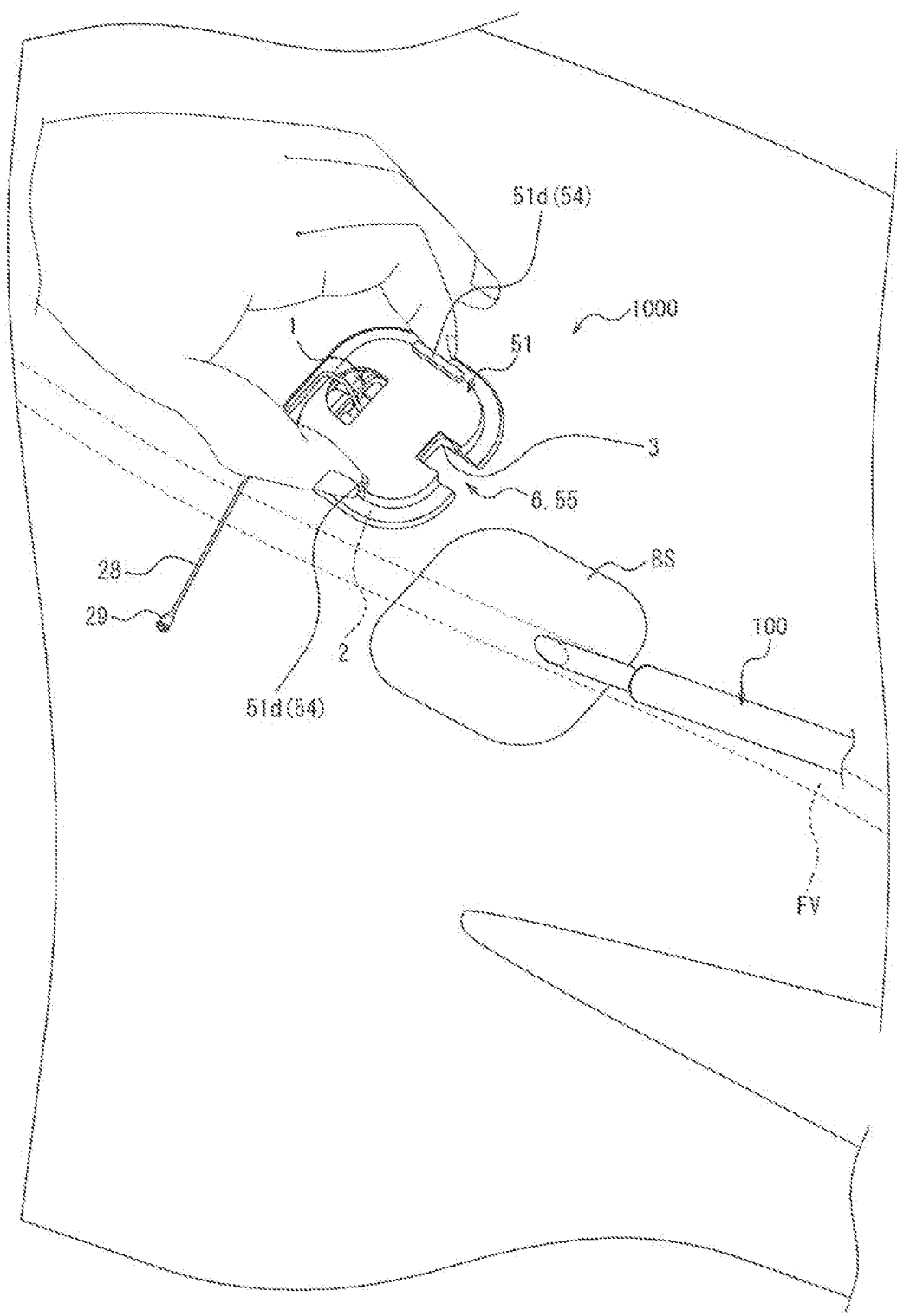
FIG. 12A is a diagram showing an outline of a cover attaching step in FIG. 11.
Figure 12B:
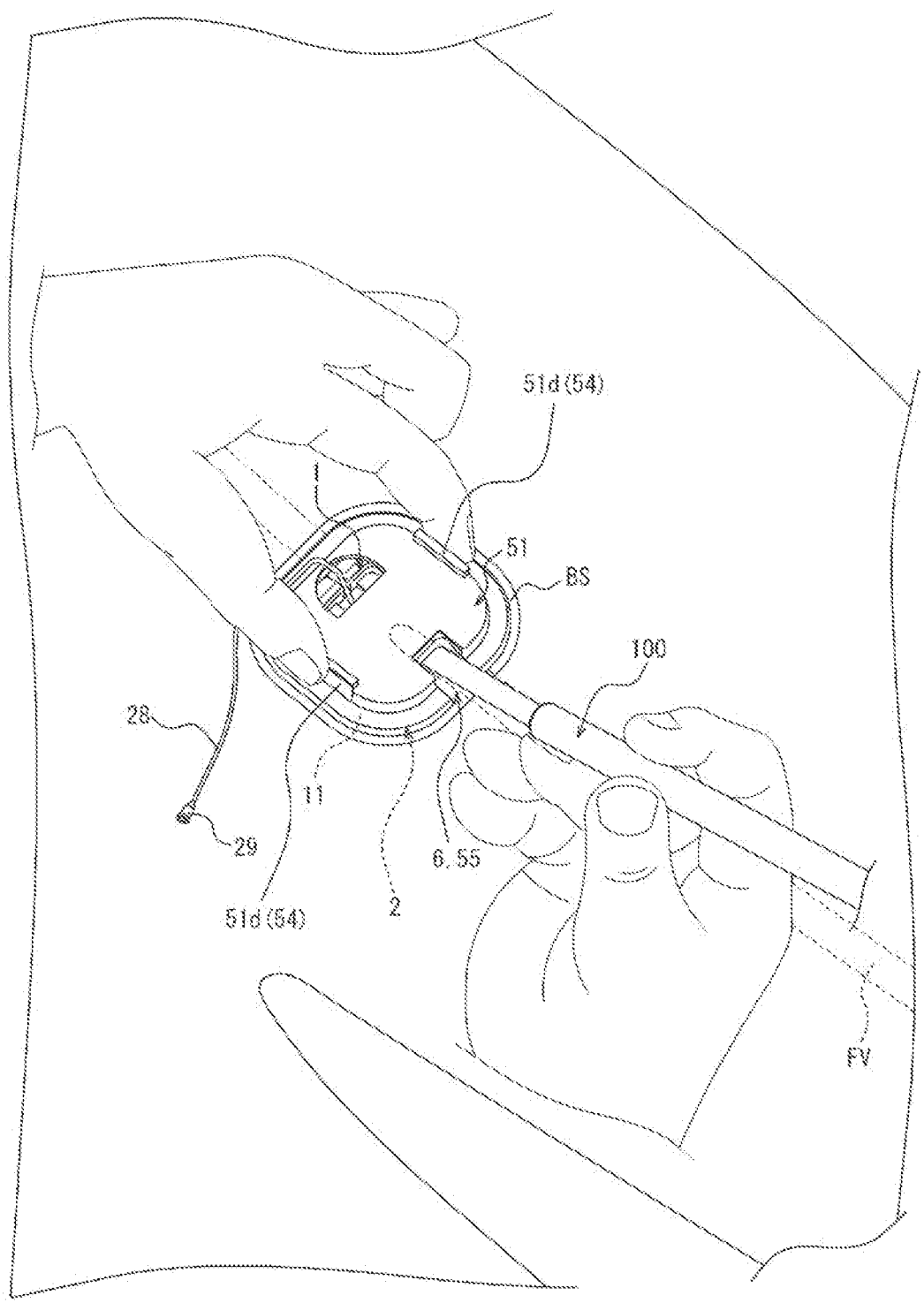
FIG. 12B is a diagram showing an outline of an adhering step in FIG. 11.
Figure 12C:
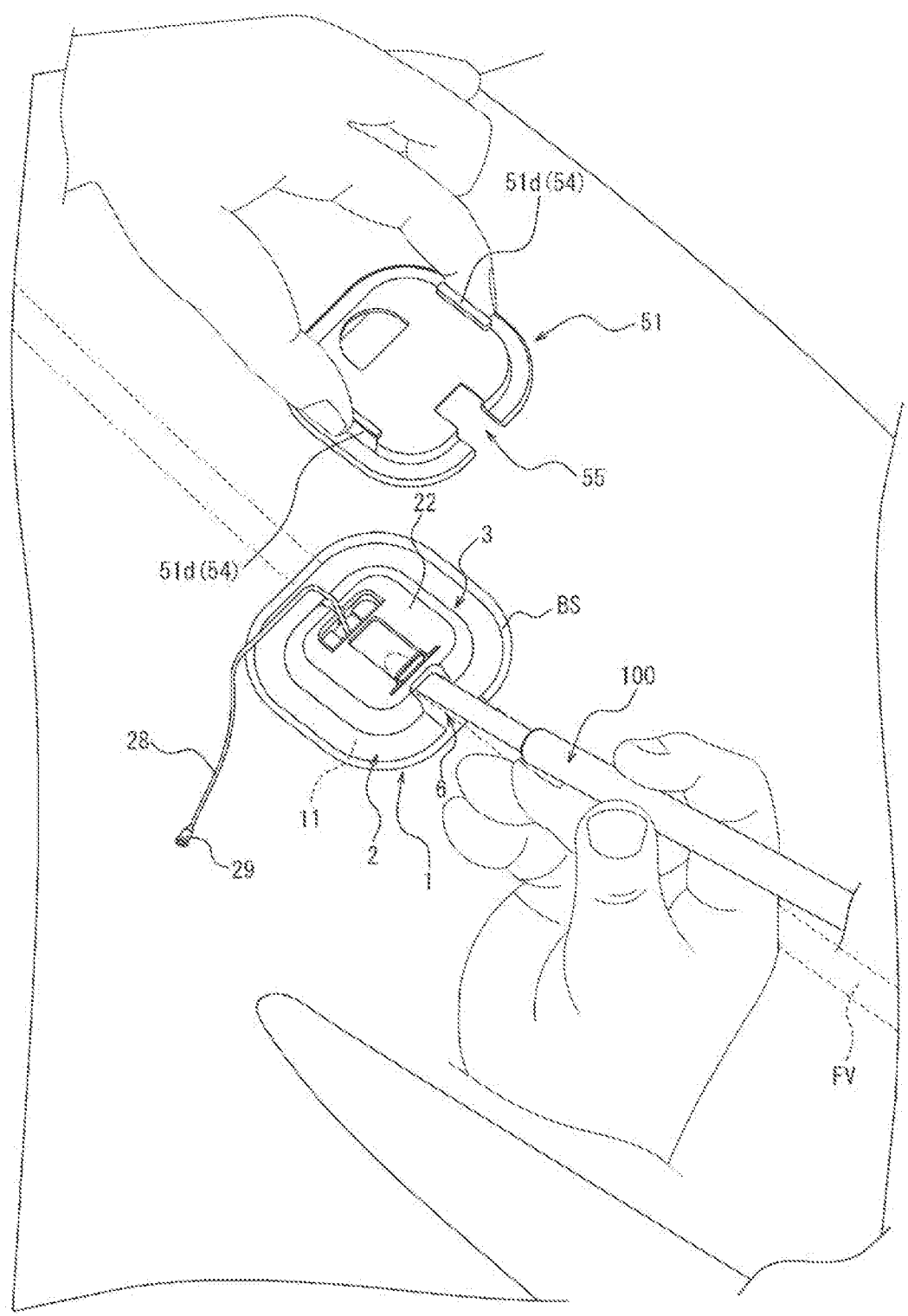
FIG. 12C is a diagram showing an outline of a cover detaching step in FIG. 11.
Figure 12D:
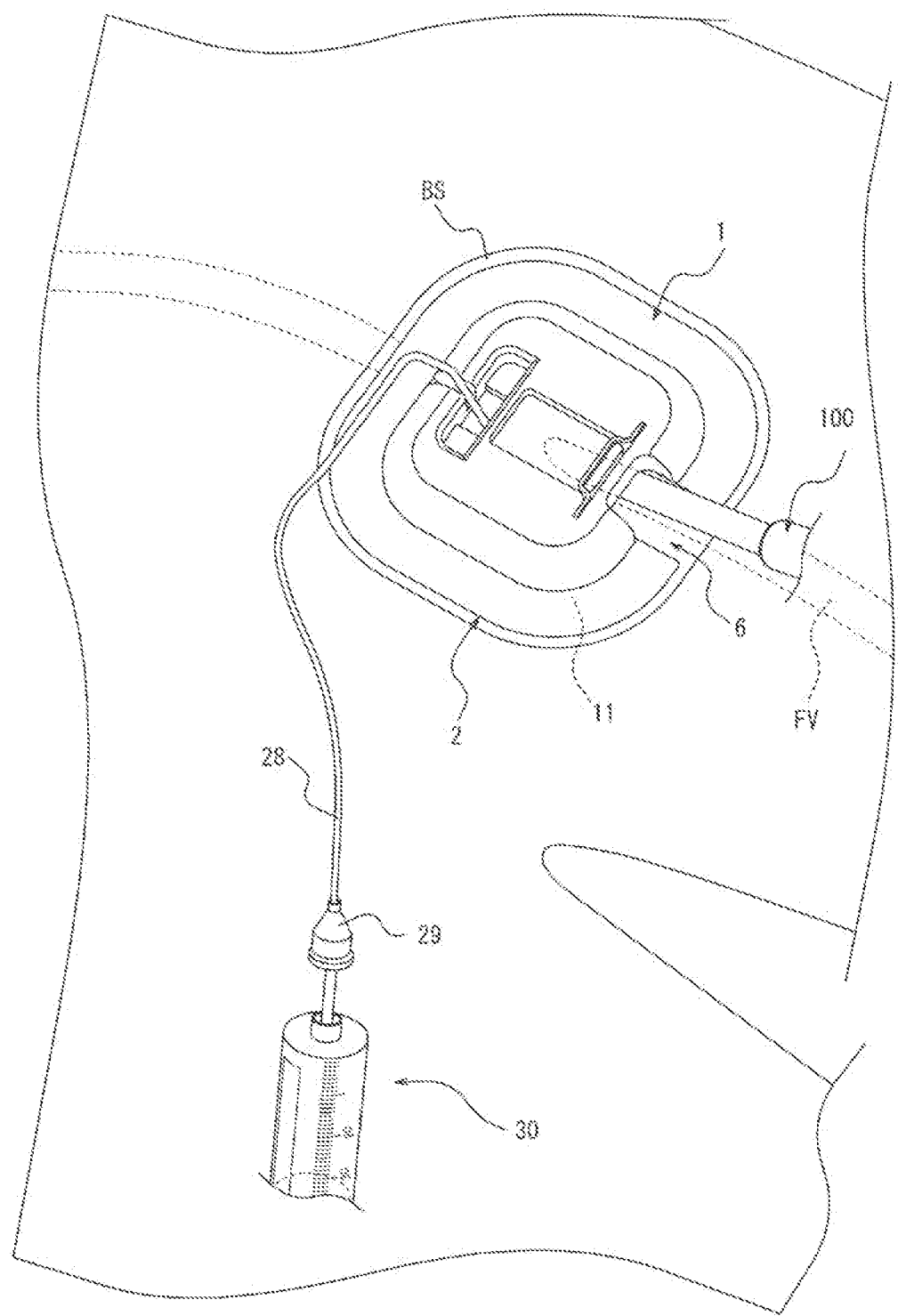
FIG. 12D is a diagram showing an outline of a first compression step in FIG. 11.
Figure 12E:
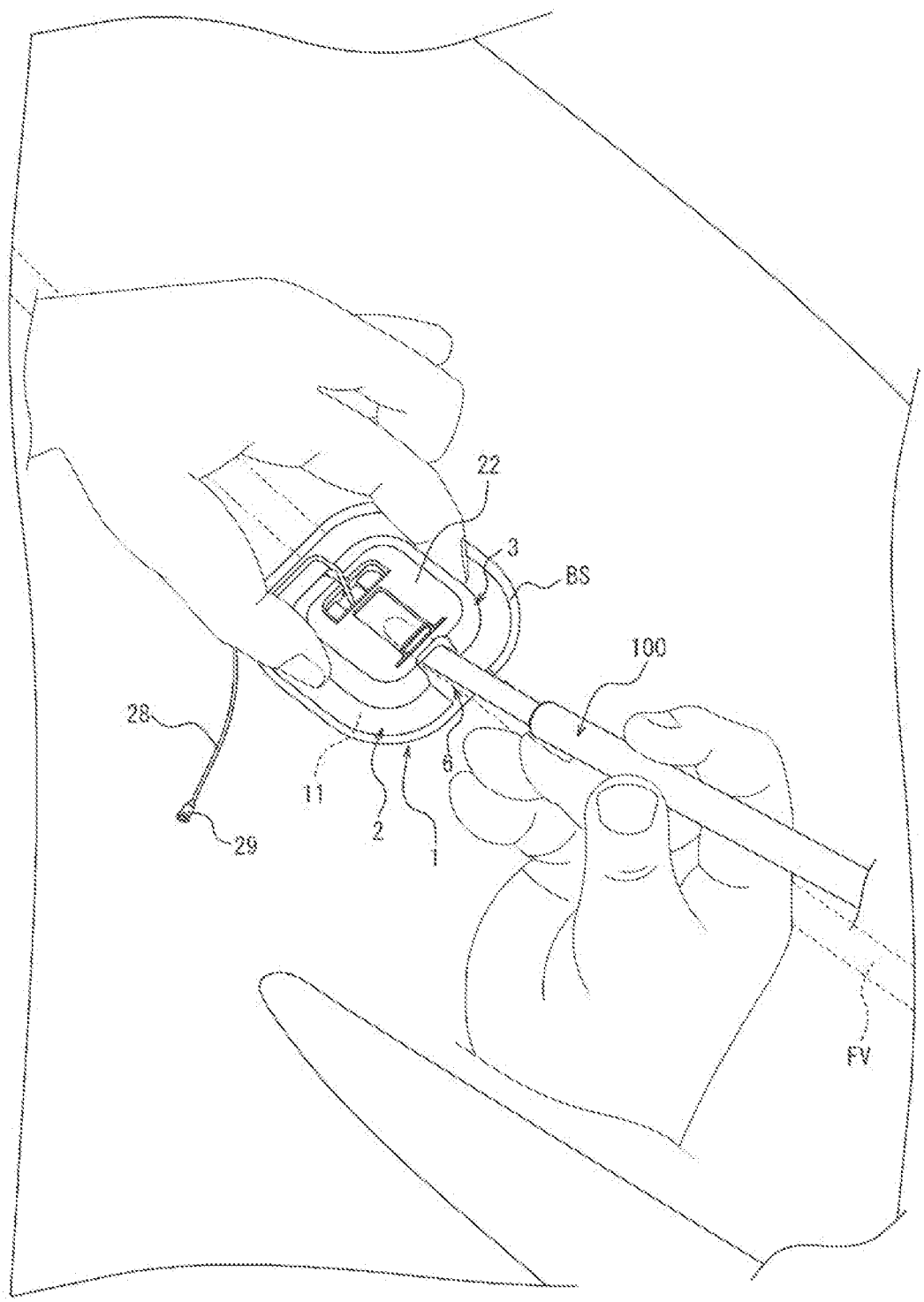
FIG. 12E is a diagram showing an outline of a removing step in FIG. 11.
Figure 12F:
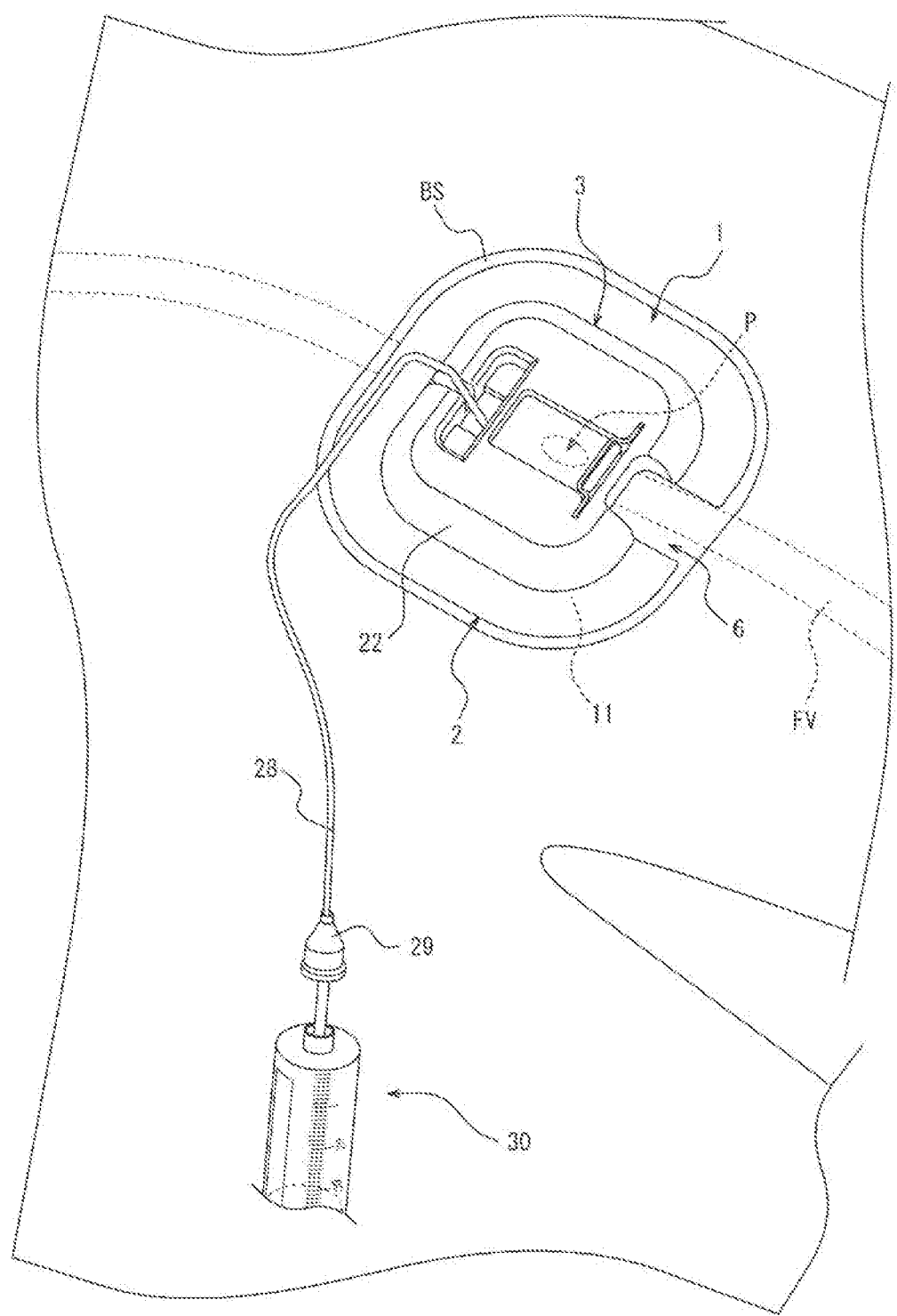
FIG. 12F is a diagram showing an outline of a second compression step in FIG. 11.

Next, a method for compressing a biological surface using the compression device 1, the method including an example of a method for attaching a compression device according to this disclosure (Hereinafter, referred to as a "device attaching method"), will be described. FIG. 11 is a flowchart showing an example of a method for compressing a biological surface. The compression method shown in FIG. 11 includes a cover attaching step S1, an adhering step S2, a cover detaching step S3, a first compression step S4, a removing step S5, and a second compression step S6. FIG. 12A is a diagram showing an outline of the cover attaching step S1. FIG. 12B is a diagram showing an outline of the adhering step S2. FIG. 12C is a diagram showing an outline of the cover detaching step S3. FIG. 12D is a diagram showing an outline of the first compression step S4. FIG. 12E is a diagram showing an outline of the removing step S5. FIG. 12F is a diagram showing an outline of the second compression step S6.

Figure 13A:
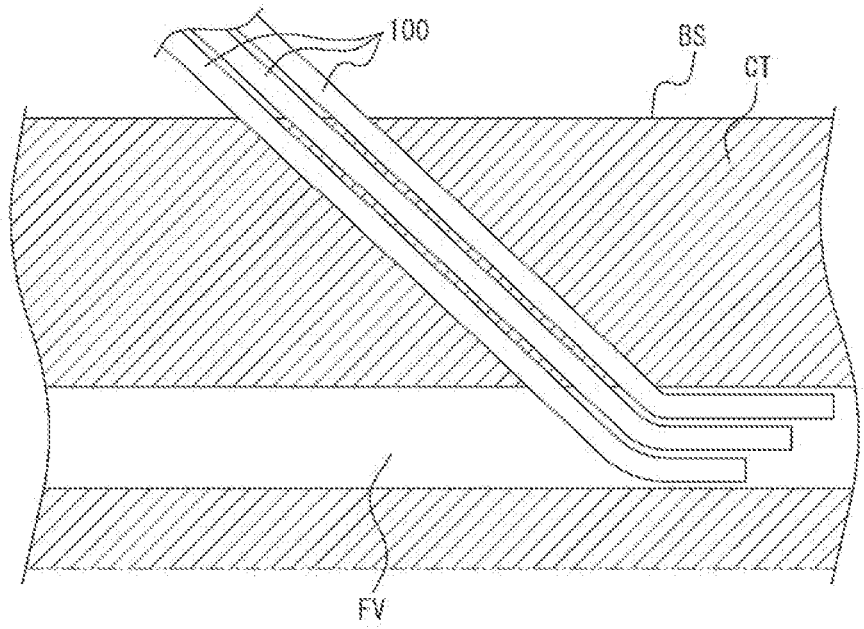
FIG. 13A is a diagram showing a state in which a medical insertion member is inserted into a femoral vein from a biological surface through a connective tissue.
Figure 13B:
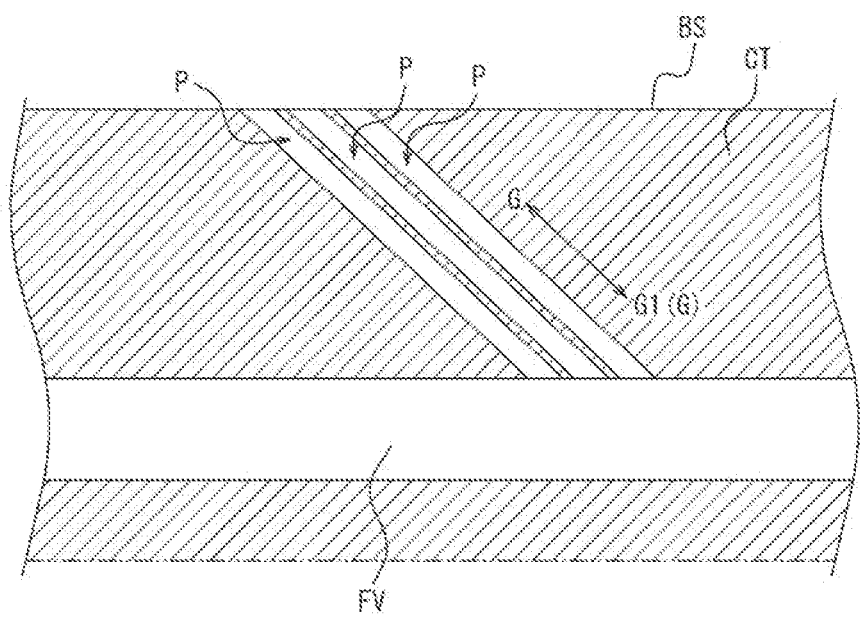
FIG. 13B is a diagram showing a state after the medical insertion member is removed from the state shown in FIG. 13A.

The compression method shown in FIGS. 11 to 12F is a method for compressing a biological surface BS to narrow or obstruct a perforation leading from the biological surface to a vein without obstructing the vein. The perforation is formed by removing a sheath as a medical device 100 in a state of being inserted into a vein such as a femoral vein from the biological surface BS through connective tissue. By the compression method shown here, bleeding can be stopped after the sheath as the medical device 100 is removed. First, the perforation formed after the medical device 100 is removed will be described with reference to FIGS. 13A and 13B. FIG. 13A shows a state in which the sheath as the medical device 100 is inserted into or positioned in a femoral vein FV from the biological surface BS through connective tissue CT. FIG. 13A shows three sheaths as the medical devices 100, and the number of sheaths may be two or less, or may be four or more. FIG. 13B shows a state after the sheaths as the medical devices 100 are removed from the state shown in FIG. 13A. As shown in FIG. 13B, when the sheaths as the medical devices 100 are removed, the perforations P are formed between the biological surface BS and the femoral vein FV. In the compression method shown in FIGS. 11 to 12F, the perforations P can be narrowed or obstructed without obstructing the femoral vein FV. Therefore, even when bleeding from a vein located at a deep position from the biological surface is stopped, bleeding can be stopped relatively efficiently without narrowing or obstructing the vein itself. Hereinafter, the details of the steps S1 to S6 will be described with reference to FIGS. 12A to 12F.

FIG. 12A shows a state in which the cover member 51 is attached to the compression member 3 of the compression device 1. As described above, the cover member 51 can be attached to the compression device 1 by covering the compression device 1 from above. In addition, as described above, the cover member 51 according to the present embodiment is attached to the compression member 3 of the compression device 1 while in contact with the entire upper surface of the peripheral portion 13 (see FIG. 3 or the like) of the adhesive sheet 2. Further, FIG. 12A shows a state in which the sheath as the medical device 100 is inserted from the biological surface BS into the femoral vein FV (see FIGS. 13A and 13B).

FIG. 12B shows a state in which the compression device 1, to which the cover member 51 is attached, is attached at a predetermined position on the biological surface BS in a state in which the sheath as the medical device 100 is inserted into or positioned in the living body.

FIG. 12C shows a state in which the cover member 51 is detached from the compression device 1 after the compression device 1 is attached to the biological surface BS.

FIGS. 12A to 12C show the use state of the compression device 1 after the release sheet 4 (see FIG. 1 or the like) is released from the adhesion surface 11.

As shown in FIGS. 12A and 12B, the compression device 1 is covered with the cover member 51, and is adhered to the biological surface BS in a state in which the cover member 51 is integrated. Specifically, as shown in FIG. 12B, the adhesion surface 11 of the adhesive sheet 2 is adhered to the biological surface BS in a state in which a portion of the sheath as the medical device 100 inserted into the living body from the biological surface BS, the portion being exposed to the outside from the biological surface BS, is received by the receiving portion 6 of the compression device 1 and the receiving portion 55 of the cover member 51.

When the compression device 1 is adhered to the biological surface BS by using the cover member 51, the second portion X2 (see FIG. 3 or the like) of the adhesive sheet 2 of the compression device 1 can also be pressed toward the biological surface BS by the cover member 51. Accordingly, the second portion X2 of the adhesive sheet 2 can be easily adhered to the biological surface BS. More specifically, according to the present embodiment, the entire region of the peripheral portion 13 (see FIG. 3 or the like) of the adhesive sheet 2 can be pressed toward the biological surface BS via the cover member 51, and the entire region of the peripheral portion 13 can be adhered to the biological surface BS. That is, according to one manner of use, the entirety of the peripheral portion 13 of the adhesive sheet 2 is pressed toward the biological surface BS through use of the cover member 51, thus adhering the entirety of the peripheral portion 13 to the biological surface BS.

As shown in FIG. 12C, after the compression device 1 is attached to the predetermined position on the biological surface BS, the cover member 51 is detached from the compression device 1. As described above, when the cover member 51 is deformed such that the pair of gripping portions 54 come close to each other, the distance between the clamping portions 52 (see FIG. 10 or the like) can be increased. Accordingly, the clamping portion 52 of the cover member 51 can be changed from a state in which the holding body 22 of the compression device 1 is clamped to a state in which the holding body 22 is not clamped. Therefore, the cover member 51 can be detached from the compression device 1. Alternatively, the cover member 51 may be detached from the compression device 1 without using the pair of gripping portions 54. The cover member 51 may be detached from the compression device 1 by pulling up the cover member 51 against a frictional force between parts at which the cover member 51 and the compression device 1 come into contact with each other.

Next, as shown in FIG. 12D, a syringe 30 as the fluid supply device is connected to the connection portion 29 of the tube 28. Through the tube 28, air is supplied to the internal spaces 40a (see FIG. 6) of the inflatable body 40 to inflate the inflatable body 40. Accordingly, before the sheath as the medical device 100 is removed from the biological surface BS, the vicinity of a wound on the biological surface BS can be compressed in advance. In other words, compression on the biological surface BS is started in a state in which the sheath as the medical device 100 is inserted into the femoral vein FV as a vein from the biological surface BS through the connective tissue CT (see FIGS. 13A and 13B). Accordingly, the medical device 100 is compressed before being removed from the biological surface BS. Accordingly, immediately after the sheath as the medical device 100 is removed, the biological surface BS can be compressed. Therefore, the perforations P (see FIG. 13B) extending from the biological surface BS to the femoral vein FV (see FIGS. 13A and 13B) can be narrowed or obstructed immediately after the sheaths are removed.

Next, as shown in FIG. 12E, the sheath as the medical device 100 is removed from the biological surface BS. The perforations P shown in FIG. 13B are formed by removing the sheaths. When the biological surface BS is not compressed at all in this state, bleeding from the femoral vein FV to the outside of the living body through the perforations P and the wound on the biological surface BS occurs. However, in the compression method shown here, as shown in FIG. 12D, the biological surface BS is compressed in advance before the sheath as the medical device 100 is removed from the biological surface BS. Therefore, the biological surface BS can be compressed to narrow or obstruct the perforations P (see FIG. 13B) immediately after the sheaths are removed, and the amount of bleeding immediately after the sheaths are removed can be reduced.

Next, as shown in FIG. 12F, the syringe 30 as the fluid supply device is connected again to the connection portion 29 of the tube 28. Air is supplied again to pressurize the internal spaces 40a of the inflatable body 40 of the compression device 1 through the tube 28, or the air is evacuated from the internal spaces 40a to reduce the pressure. In other words, the compression force on the biological surface BS is adjusted after the sheath as the medical device 100 is removed. Accordingly, by adjusting the compression force on the biological surface BS and further narrowing or obstructing the perforations P (see FIG. 13B) without obstructing the femoral vein FV (see FIGS. 13A and 13B), the amount of bleeding can be greatly reduced or the bleeding can be stopped.

More specifically, when the bleeding is confirmed after the sheaths are removed, the compression force is slowly increased to increase the pressure until the bleeding is stopped. On the other hand, when the bleeding is confirmed to be stopped after the sheaths are removed, the compression force is slowly reduced to reduce the pressure until the bleeding is confirmed. After the bleeding is confirmed, the compression force is slowly increased to pressurize until the bleeding is stopped. Accordingly, it is possible to prevent the obstruction of the femoral vein FV (see FIGS. 13A and 13B) due to excessive pressurization.

Whether the biological surface BS is appropriately compressed may be detected using an ultrasonic device. Specifically, the inflatable body 40 as the expander 21 (see FIG. 6 or the like) and the holding body 22 are formed of a material having ultrasonic transmissibility, and a fluid having ultrasonic transmissibility such as water is supplied to the inflatable body 40. Accordingly, a compression state made by the compression device 1 can be diagnosed by ultrasounds. That is, the ultrasonic device can detect whether the femoral vein FV (see FIGS. 13A and 13B) is obstructed. The compression force of the compression device 1 may be adjusted based on a diagnosis result by the ultrasonic device.

By maintaining the compression state for several hours (for example, 2 to 6 hours) as it is, the bleeding can be stopped. After the bleeding is stopped, the compression device 1 is detached from the biological surface BS by releasing the adhesion surface 11 of the adhesive sheet 2 from the biological surface BS.

In the compression method shown here, the perforations P (see FIG. 13B) are narrowed or obstructed without obstructing the femoral vein FV (see FIGS. 13A and 13B). When stopping the bleeding from the vein, the bleeding can be stopped by narrowing or obstructing the perforations P (see FIG. 13B). On the other hand, for example, when stopping bleeding from a femoral artery, even when only the perforations are obstructed, the blood leaks and spreads in the connective tissue CT (see FIGS. 13A and 13B), and thus the bleeding cannot be stopped. When stopping the bleeding from the femoral artery, it is necessary to take a large measure, such as a method for strongly compressing the artery itself until the artery is narrowed or obstructed, or a method for obstructing a hole of an artery wall.

Therefore, in the above-mentioned compression method, it is preferable to compress the biological surface BS to a position at which a compression depth from the biological surface BS is 5 mm to 20 mm. By setting the compression depth within the above-mentioned range, it is easy to implement the compression state in which the perforations P (see FIG. 13B) are narrowed or obstructed without obstructing the vein. The compression depth is more preferably 5 mm to 15 mm, and even more preferably 8 mm to 12 mm.

In the above-mentioned compression method, it is preferable to compress the biological surface BS at 10 g/cm$^2$ to 600 g/cm$^2$ from the biological surface BS. Compression pressure is pressure after the sheath as the medical device 100 is removed, and does not mean the above-mentioned compression force before the sheath is removed. By setting the compression pressure in the above-mentioned range, it is easy to implement the compression state in which the perforations P (see FIG. 13B) are narrowed or obstructed without obstructing the vein. The compression pressure is more preferably 50 g/cm$^2$ to 400 g/cm$^2$, and even more preferably 100 g/cm$^2$ to 300 g/cm$^2$.

It is preferable to compress the biological surface BS along a direction orthogonal to an extending direction of the perforations P (see FIG. 13B). The phrase "compressing the biological surface BS along a direction orthogonal to an extending direction of the perforations" means not only compressing only in the direction orthogonal to the extending direction of the perforations but also compressing in a direction inclined at an angle equal to or less than a predetermined angle (for example, 30 degrees or less) with respect to the direction orthogonal to the extending direction of the perforations. The compression device 1 according to the present embodiment can compress the biological surface BS along the direction orthogonal to the extending direction of the perforations P (see FIG. 13B).

Figure 14:
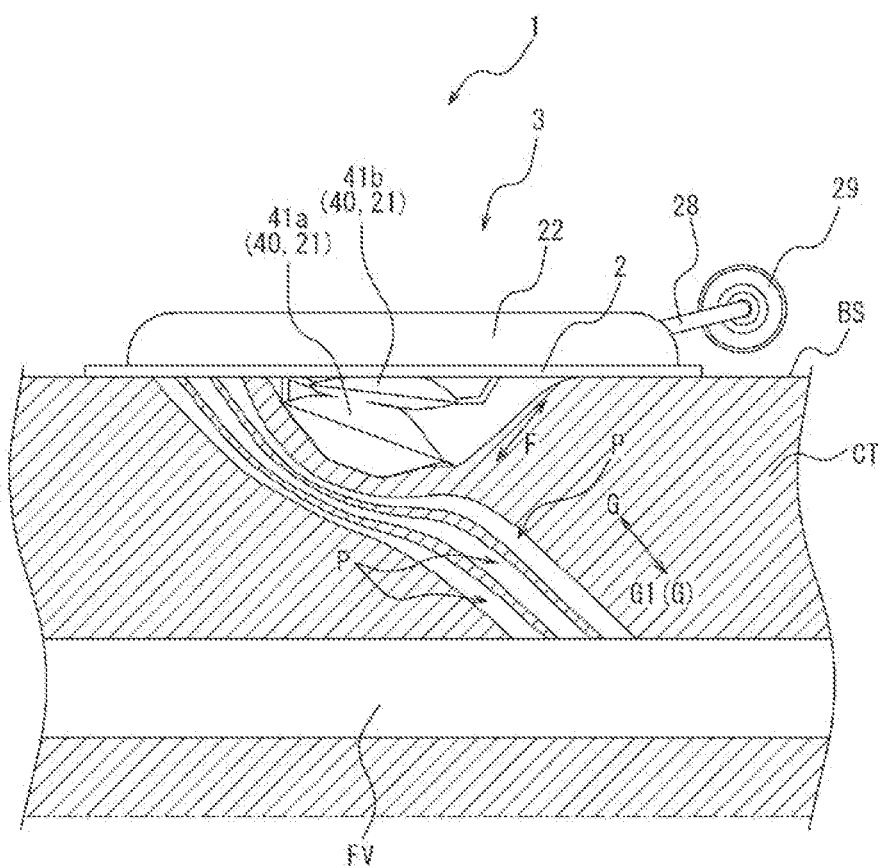
FIG. 14 is a diagram showing a state in which perforations shown in FIG. 13B are narrowed or obstructed by the compression device shown in FIG. 1.

Specifically, the first inflatable portion 41a and the second inflatable portion 41b of the inflatable body 40 according to the present embodiment are inflated toward the direction inclined with respect to the sheet thickness direction A, as described above. Accordingly, the biological surface can be compressed along the direction orthogonal to the extending direction of the perforations P (see FIG. 13B). Specifically, as shown in FIGS. 13A and 13B, the sheath as the medical device 100 is inserted not in a direction orthogonal to the biological surface BS (the same direction as the sheet thickness direction A) but in a direction inclined to one side with respect to the direction orthogonal to the biological surface BS. Therefore, as shown in FIG. 13B, the extending direction of the perforations P is also inclined with respect to the direction orthogonal to the biological surface BS. Therefore, when the first inflatable portion 41a and the second inflatable portion 41b can be inflated in a direction inclined to a side opposite to the extending direction of the perforations P (hereinafter, may be referred to as an "inclination direction F") with respect to the sheet thickness direction A which is the direction orthogonal to the biological surface BS, the biological surface BS is easily compressed along the direction orthogonal to the extending direction of the perforations P. Accordingly, it is easy to implement the compression device 1 that narrows or obstructs the perforations P without obstructing the vein such as the femoral vein FV in FIGS. 13A and 13B. FIG. 14 is a diagram showing the state in which the perforations P shown in FIG. 13B are narrowed or obstructed by the compression device 1. As shown in FIG. 14, the perforations P are more easily narrowed or obstructed without further obstructing the vein such as the femoral vein FV by the compression device 1.

According to the compressing method shown in FIGS. 11 to 12F, the bleeding can be stopped by narrowing or obstructing the perforations P (see FIG. 13B) without obstructing the vein such as the femoral vein FV. In particular, by implementing the compression method using the compression device 1, it is possible to stop the bleeding by a simple method without compression by a hand of the health care worker or using a large-scale hemostasis device.

<Compression of Compression Device 1 on Biological Surface>

As shown in FIG. 14, in the compression device 1, the inflatable body 40 of the compression member 3 can compress the biological surface toward the inclination direction F inclined with respect to a vertical direction (in FIG. 14, the vertical direction is the same direction as the sheet thickness direction A, and is an upward-downward direction in FIG. 14. Hereinafter, it is simply referred to as a "vertical direction") perpendicular to the biological surface BS in a state in which the adhesive sheet 2 is attached to the living body. Accordingly, as shown in FIG. 14, the perforations P are easily narrowed or obstructed without obstructing the vein such as the femoral vein FV.

Figure 15:
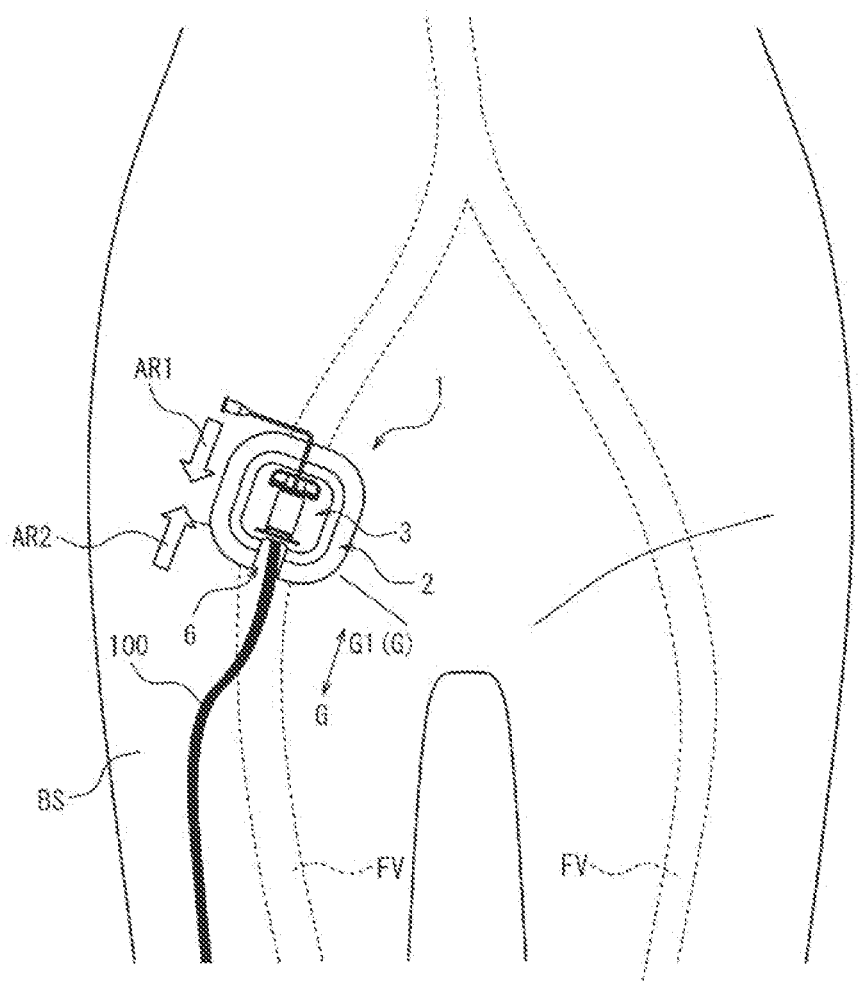
FIG. 15 is a front view of the state shown in FIG. 14 as seen from a biological surface side.

FIG. 15 is a front view of the state shown in FIG. 14 as seen from a biological surface BS side. In other words, FIG. 15 shows a front view of the biological surface BS at a position compressed by the compression device 1. Here, the phrase "front view of the biological surface at a position compressed by the compression device" means a state in which a portion of the biological surface to be compressed by the compression device is seen from a direction perpendicular to the portion before the compressing. FIG. 15 shows a front view of an inguinal region. In the front view shown in FIG. 15, a direction in which the biological surface BS is compressed (see a white arrow "AR1" in FIG. 15) is opposite to an insertion direction G1 (see a white arrow "AR2" in FIG. 15) of the sheath from the biological surface BS toward the vein in an extending direction G of the perforations P. That is, the direction in which the compression device 1 compresses the biological surface BS is opposite to the insertion direction G1 of the sheath in the front view shown in FIG. 15. Accordingly, the perforations P (see FIGS. 13B and 14) are easily narrowed or obstructed without obstructing the vein such as the femoral vein FV.

In other words, as shown in FIG. 14, the extending direction G of the perforations P is inclined with respect to the biological surface BS and is also inclined with respect to the vertical direction (upward-downward direction in FIG. 14) perpendicular to the biological surface BS. In addition, as shown in FIG. 14, a compression direction of the compression device 1 on the biological surface BS is also inclined with respect to the biological surface BS and also inclined with respect to the vertical direction (upward-downward direction in FIG. 14) perpendicular to the biological surface BS. Further, as shown in FIG. 14, the extending direction G of the perforations P is inclined to the side opposite to the inclination direction F as the compression direction of the compression device 1 on the biological surface with respect to the vertical direction (upward-downward direction in FIG. 14). That is, the compression of the compression device 1 on the biological surface is executed such that the compression direction intersects with the extending direction G of the perforations P. Accordingly, the perforations P can be efficiently narrowed or obstructed.

Figure 16:
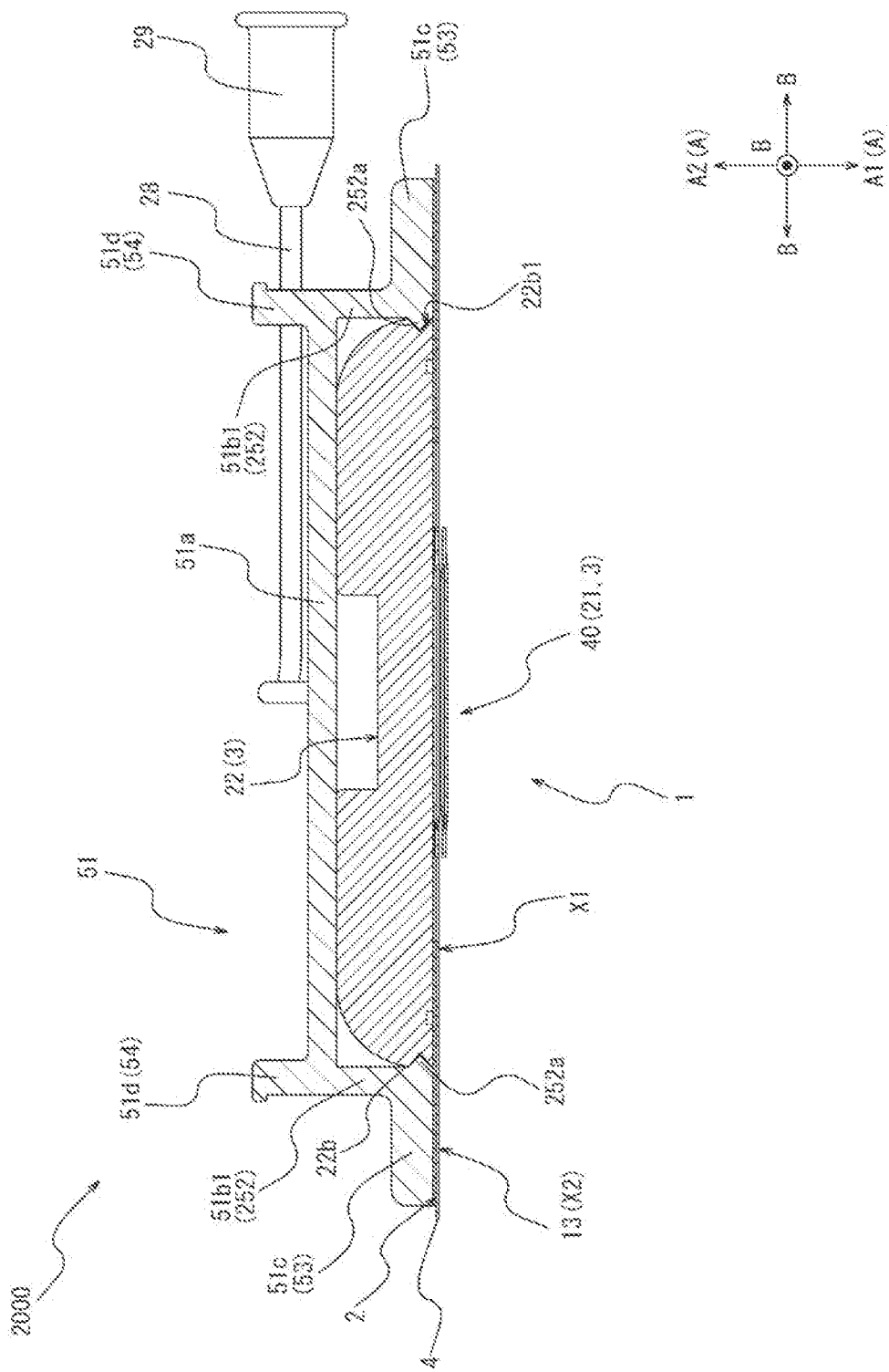
FIG. 16 is a view showing a modification of the compression device set shown in FIG. 1.

The compression device set and the method for attaching the device according to this disclosure are not limited to the specific configurations and the steps shown in the embodiment, and various modifications and changes may be made without departing from the description of the claims. FIG. 16 is a view showing a compression device set 2000 as a modification of the compression device set 1000.

The compression device set 2000 shown in FIG. 16 differs from the compression device set 1000 (see FIG. 1 or the like) in terms of the structure or configuration for locking a cover member to a compression device. Other aspects and features of the compression device are the same as described above and a detailed description of such features and aspects is not repeated. Therefore, differences between the compression device set 2000 and the compression device set 1000 (see FIG. 1 or the like) will be mainly described here.

FIG. 16 is a cross-sectional view of the compression device set 2000 in an attached state. FIG. 16 is the section view of the compression device set 2000 at the same position as the cross section of the compression device set 1000 shown in FIG. 10 (see FIG. 1 or the like). As shown in FIG. 16, the cover member 51 includes a side-end engaging portion 252. The side-end engaging portion 252 engages with the opposite portions of the side end surface 22b of the holding body 22 of the compression device 1, respectively. In an example shown in FIG. 16, the side-end engaging portion 252 is constituted by the pair of first plate portions 51b1 of the cover member 51.

Here, the side-end engaging portion 252 of the cover member 51 is provided with convex portions 252a (projecting portions or projections). In addition, concave portions 22b1 (recessed portions or recesses) or hole portions (holes) that are fitted with the convex portions 252a are provided at the opposite portions of the side end surface 22b of the holding body 22. In the example shown in FIG. 16, by changing the facing distance (distance between left and right sides in FIG. 16) of the pair of gripping portions 54, it is possible to switch between a locking position at which the convex portions 252a are fitted into the concave portions 22b1 and a locking release position at which the convex portions 252a are not fitted into the concave portions 22b1.

More specifically, the cover member 51 according to the present embodiment is provided with the convex portions 252a on facing surfaces of the pair of first plate portions 51b1. The concave portions 22b1 are formed at the opposite portions of the side end surface 22b of the holding body 22 sandwiched between the pair of first plate portions 51b1. In place of or in addition to the locking by the clamping, by providing such fitted concave and convex portions, a locked state between the cover member 51 and the compression device 1 can be further stabilized.

In the example shown in FIG. 16, the cover member 51 is provided with the convex portions 252a, and the compression device 1 is provided with the concave portions 22b1, but this disclosure is not limited to this configuration. The cover member 51 may be provided with concave portions, and the compression device 1 may be provided with convex portions. In addition, the cover member 51 may be provided with both a convex portion and a concave portion, and the compression device 1 may be provided with a concave portion to be fitted with the convex portion of the cover member 51 and a convex portion to be fitted into the concave portion of the cover member 51. That is, as long as the locked state of the cover member 51 and the compression device 1 is implemented by fitting the side-end engaging portion 252 of the cover member 51 with the side end surface 22b of the holding body 22 of the compression device 1 at the concave and convex portions, a shape or the like of the concave and convex portions is not particularly limited.

The cover member 51 shown in FIG. 16 is also provided with the sheet cover portion 53 that protrudes from the side-end engaging portion 252 in the sheet in-plane direction B, as in the embodiment. The sheet cover portion 53 comes into contact with the upper surface of at least a part of the second portion X2 of the adhesive sheet 2 (the entire region of the peripheral portion 13 in the example shown in FIG. 16) in a state in which the side-end engaging portion 252 engages with the opposite portions of the side end surface 22b of the holding body 22.

The detailed description above describes embodiments of a compression device set and a compression device attachment method representing examples of the compression device set and compression device attachment method disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST 1 compression device
2 adhesive sheet
3 compression member
4 release sheet
6 receiving portion
11 adhesion surface
12 attaching surface
13 peripheral portion
21 expander
21a contact portion
21b pressing portion
22 holding body
22a through hole
22b side end surface
22b1 concave portion
22c locking protrusion
28 tube
29 connection portion
30 syringe
40 inflatable body
40a internal space
41a first inflatable portion
41a1 first internal space
41b second inflatable portion
41b1 second internal space
42 extending portion
51 cover member
51a ceiling plate portion
51a1 ceiling plate opening
51b peripheral wall portion
51b1 first plate portion
51b2 second plate portion
51c flange plate portion
51d gripping plate portion
52 clamping portion
53 sheet cover portion
54 gripping portion
55 receiving portion
100 medical device
252 side-end engaging portion
252a convex portion
1000, 2000 compression device set
A sheet thickness direction
A1 downward direction
A2 upward direction
B sheet in-plane direction
F inclination direction
G extending direction of perforation
G1 insertion direction of sheath
H in-plane direction of biological surface
BS biological surface
CT connective tissue
FV femoral vein
P perforation
X1 first portion of adhesive sheet
X2 second portion of adhesive sheet

What is claimed is:

1. A compression device set comprising:
   a compression device that is configured to be adhered to a biological surface and that is configured to compress the biological surface; and
   a cover member configured to be attached to and detached from the compression device, the compression device including:
      an adhesive sheet possessing a lower surface and possessing an upper surface side, the lower surface of the adhesive sheet being an adhesion surface configured to be adhered to the biological surface;
      a compression member that is fixed to the adhesive sheet on the upper surface side of the adhesive sheet and that is configured to compress the biological surface in a state in which the adhesion surface of the adhesive sheet is adhered to the biological surface;
      the adhesive sheet including a first portion that is in contact with the compression member and a second portion that is not in contact with the compression member; and
      the cover member being configured to be attached to the compression member so that the cover member contacts an upper surface of at least a part of the second portion of the adhesive sheet.

2. The compression device set according to claim 1, wherein
   the compression member of the compression device includes:
      an expander that is expandable; and
      a holding body configured to hold the expander to be expandable in a sheet thickness direction of the adhesive sheet, and
   the cover member being configured to be attached to the holding body.

3. The compression device set according to claim 2, wherein
   the second portion of the adhesive sheet includes a peripheral portion located outside an outer edge of the holding body in a plan view seen in the sheet thickness direction, and
   the cover member is configured to be attached to the holding body in a state in which the cover member is configured to come into contact with an upper surface of the entire peripheral portion.

4. The compression device set according to claim 2, wherein
   the cover member is locked to the holding body by a part of the cover member engaging with a side end surface of the holding body, the side end surface being located in a sheet in-plane direction orthogonal to the sheet thickness direction.

5. The compression device set according to claim 4, wherein
   the cover member includes:
      a clamping portion configured to clamp opposite portions of the side end surface of the holding body; and
      a sheet cover portion that protrudes from the clamping portion in the sheet in-plane direction and that is configured to come into contact with the upper surface of at least a part of the second portion of the adhesive sheet in the state in which the clamping portion clamps the opposite portions of the side end surface of the holding body.

6. The compression device set according to claim 5, wherein
   the cover member includes a pair of gripping portions extending from the clamping portion in the sheet thickness direction, the pair of gripping portions being spaced apart by a facing distance, and
   the gripping portions being configured to be gripped and released by a user to change the facing distance between the pair of gripping portions and thereby switch the cover member between a locking position in which the clamping portion clamps the opposite portions of the side end surface of the holding body and a locking release position in which the clamping portion does not clamp the opposite portions of the side end surface of the holding body.

7. The compression device set according to claim 4, wherein the cover member includes:
 a side-end engaging portion that engages with opposite portions of the side end surface of the holding body; and
 a sheet cover portion that protrudes from the side-end engaging portion in the sheet in-plane direction and that is configured to come into contact with the upper surface of at least a part of the second portion of the adhesive sheet in a state in which the side-end engaging portion engages with the opposite portions of the side end surface of the holding body,
 one of the side-end engaging portion and the opposite portions of the side end surface of the holding body including a convex portion, and
 the other one of the side-end engaging portion and the opposite portions of the side end surface of the holding body including a concave portion or a hole in which is fitted the convex portion.

8. The compression device set according to claim 7, wherein the cover member includes a pair of gripping portions each extending in the sheet thickness direction from the side-end engaging portion, the pair of gripping portions being spaced apart by a facing distance, and
the gripping portions being configured to be gripped and released by a user to change the facing distance between the pair of gripping portions and thereby switch the cover member between a locking position at which the convex portion is fitted into the concave portion or the hole and a locking release position at which the convex portion is not fitted into the concave portion or the hole.

9. A compression device set comprising:
a compression member and a cover member;
the compression member comprising an adhesive sheet, a holding member and an inflatable body:
the adhesive sheet possessing an upper surface and also possessing a lower surface that is an adhesion surface configured to adhere the adhesive sheet to a biological surface;
the holding member being fixed to the upper surface of the adhesive sheet so that a portion of the upper surface of the adhesive sheet is in contact with the holding member, the holding member possessing a lower surface that faces toward the biological surface when the adhesive sheet is adhered to the biological surface;
the inflatable body being fixed to the holding member and being positioned in underlying relation to the lower surface of the holding member so that the inflatable body is located between the lower surface of the holding member and the biological surface when the adhesive sheet is adhered to the biological surface, the inflatable body having an interior and an outer surface, the inflatable body being expandable upon introducing a fluid into the interior of the inflatable body to press the outer surface of the inflatable body against a portion of the biological surface and apply a compression force to the portion of the biological surface when the adhesive sheet is adhered to the biological surface;
the cover member being attachable to the compression member, the cover member including a surface configured to contact a part of the compression member when the cover member is attached to the compression member so that a force applied to the cover member is transmitted to the adhesive sheet of the compression member to press the adhesion surface of the adhesive sheet into adhering contact with the biological surface.

10. The compression device set according to claim 9, wherein the upper surface of the adhesive sheet includes a second portion that is not in contact with the holding member, the second portion of the upper surface of the adhesive sheet being located outwardly of the first portion of the upper surface of the adhesive sheet and at least partially surrounding the first portion of the upper surface of the adhesive sheet.

11. The compression device set according to claim 10, wherein the cover member includes a cover plate portion, a peripheral wall portion connected to and projecting away from the cover plate portion and a flange plate portion connected to and projecting away from the peripheral wall portion, the cover member being configured so that the flange plate portion overlies the second portion of the upper surface of the adhesive sheet when the cover member is attached to the compression member.

12. The compression device set according to claim 9, wherein the cover member includes a cover plate portion and a peripheral wall portion connected to and projecting away from the cover plate portion, the peripheral wall portion possessing an inner surface, the cover plate portion of the cover member overlying an upper surface of the holding member when the cover member is attached to the compression member, the inner surface of the peripheral wall portion of the cover member facing an outwardly facing side end surface of the holding body when the cover member is attached to the compression member.

13. The compression device set according to claim 12, wherein the cover member is configured so that the inner surface of the peripheral wall portion of the cover member contacts the outwardly facing side end surface of the holding body to attach the cover member to the compression member.

14. The compression device set according to claim 9, wherein the adhesive sheet is configured to include a central opening region as seen in a plan view so that the adhesive sheet surrounds the central opening region, the holding member extending across the central opening region, and a portion of the holding member extending across the central opening region overlying the inflatable body.

15. A method for attaching a compression device to a biological surface so that the compression device is operable to compress the biological surface,
the compression device including:
 an adhesive sheet possessing a lower surface and possessing an upper surface side, the lower surface of the adhesive sheet including an adhesion surface configured to be adhered to the biological surface;
 a compression member that is fixed to the adhesive sheet on the upper surface side of the adhesive sheet and that is configured to compress the biological surface in a state in which the adhesion surface of the adhesive sheet is adhered to the biological surface;

the adhesive sheet including a first portion that is in contact with the compression member and a second portion that is not in contact with the compression member, and the method comprising:
attaching a cover member to the compression member so that the cover member contacts an upper surface of at least a part of the second portion of the adhesive sheet; and
pressing at least a part of the second portion of the adhesive sheet toward the biological surface via the cover member, and adhering at least the part of the second portion of the adhesive sheet to the biological surface.

16. The method according to claim 15, wherein the cover member includes a cover plate portion, a peripheral wall portion projecting away from the cover plate portion and a pair of upstanding gripping portions spaced-apart from one another and projecting away from the cover plate portion, the attaching of the cover member to the compression member including gripping the pair of upstanding gripping portions and moving the cover member toward the compression member and into contact with the upper surface of at least the part of the second portion of the adhesive sheet.

17. The method according to claim 15, wherein the cover member includes a cover plate portion, a peripheral wall portion projecting away from the cover plate portion and a pair of upstanding gripping portions spaced-apart from one another and projecting away from the cover plate portion, the attaching of the cover member to the compression member including: gripping the pair of upstanding gripping portions to move portions of the peripheral wall portion away from one another; positioning the cover member so that the portions of the peripheral wall portion are adjacent to portions of the compression member; and releasing the pair of upstanding gripping portions so that the portions of the peripheral wall portion contact the portions of the compression member.

18. The method according to claim 15, wherein the cover member includes a cover plate portion and a peripheral wall portion projecting away from the cover plate portion, the attaching of the cover member to the compression member including moving portions of the peripheral wall portion into contact with portions of the compression member.

19. The method according to claim 15, wherein the compression member includes a holding body and an inflatable body, the holding body being fixed to the upper surface side of the adhesive sheet, the inflatable body being fixed to a lower surface of the holding body, the holding body including a side end surface that projects away from the upper surface side of the adhesive sheet, the attaching of the cover member to the compression member including moving portions of the cover member into contact with portions of the side end surface of the holding body.

20. The method according to claim 15, wherein the compression member includes a holding body and an inflatable body, the holding body being fixed to the upper surface side of the adhesive sheet, the inflatable body being fixed to a lower surface of the holding body, the holding body including a side end surface that projects away from the upper surface side of the adhesive sheet, the attaching of the cover member to the compression member including positioning each of plural spaced apart projections in respective recesses or holes, the projections being provided on one of the cover member and the compression member, the recesses or holes being provided on the other of the cover member and the compression member.

* * * * *